US011103416B2

(12) United States Patent
Zhadkevich

(10) Patent No.: US 11,103,416 B2
(45) Date of Patent: Aug. 31, 2021

(54) DEVICE AND METHOD FOR SIMULTANEOUS DETECTION, MONITORING AND PREVENTION OF CEREBRAL EMBOLI

(71) Applicant: Michael Zhadkevich, Inman, SC (US)

(72) Inventor: Michael Zhadkevich, Inman, SC (US)

( * ) Notice: Subject to any disclaimer, the term of this patent is extended or adjusted under 35 U.S.C. 154(b) by 1174 days.

(21) Appl. No.: 15/271,586

(22) Filed: Sep. 21, 2016

(65) Prior Publication Data

US 2017/0087045 A1 Mar. 30, 2017

Related U.S. Application Data

(60) Provisional application No. 62/233,445, filed on Sep. 28, 2015.

(51) Int. Cl.
*A61H 9/00* (2006.01)
*A61B 8/00* (2006.01)
(Continued)

(52) U.S. Cl.
CPC ......... *A61H 9/0078* (2013.01); *A61B 5/0053* (2013.01); *A61B 5/026* (2013.01);
(Continued)

(58) Field of Classification Search
CPC . A61H 7/00; A61H 7/001; A61H 9/00; A61H 9/005; A61H 9/0078; A61H 9/0092;
(Continued)

(56) References Cited

U.S. PATENT DOCUMENTS 2,271,927 A 2/1942 Saighman
2,571,461 A 10/1951 Livingston
(Continued)

FOREIGN PATENT DOCUMENTS

CN 201 356 600 Y 12/2009
EP 0109627 A1 5/1984
(Continued)

OTHER PUBLICATIONS

United States Patent and Trademark Office; Office Action; U.S. Appl. No. 15/008,276; USPTO; pp. 1-14; publisher United States Patent and Trademark Office; Published Alexandria, Virginia, USA; copyright and dated Jul. 20, 2018; copy enclosed (14 pages).
(Continued)

*Primary Examiner* — Colin W Stuart
(74) *Attorney, Agent, or Firm* — J. Bennett Mullinax LLC

(57) ABSTRACT

A device for the prevention of stroke is provided that has a processor, a compression system, a compression member, and a vascular probe carried by the compression member. The vascular probe senses a parameter of a circulation system from a closed neck artery that is not being externally accessed. The processor processes the closed parameter and based upon this processing communicates with the compression system to instruct the compression system to actuate the compression member. The compression member and vascular probe are external to the interior of the patient when the vascular probe senses the closed parameter of the circulation system.

24 Claims, 19 Drawing Sheets

(51) Int. Cl.
*A61B 8/08* (2006.01)
*A61B 5/00* (2006.01)
*A61B 8/06* (2006.01)
*A61B 5/021* (2006.01)
*A61B 17/135* (2006.01)
*A61B 5/02* (2006.01)
*A61B 5/026* (2006.01)
*A61H 1/00* (2006.01)
*A61B 17/132* (2006.01)

(52) U.S. Cl.
CPC ...... *A61B 5/02007* (2013.01); *A61B 5/02035* (2013.01); *A61B 5/02141* (2013.01); *A61B 5/4836* (2013.01); *A61B 5/6822* (2013.01); *A61B 5/6831* (2013.01); *A61B 8/06* (2013.01); *A61B 8/4227* (2013.01); *A61B 8/4477* (2013.01); *A61B 8/488* (2013.01); *A61B 8/5223* (2013.01); *A61B 17/1355* (2013.01); *A61H 1/008* (2013.01); *A61B 8/0833* (2013.01); *A61B 17/1325* (2013.01); *A61H 2201/165* (2013.01); *A61H 2205/04* (2013.01)

(58) Field of Classification Search
CPC ............ A61H 2205/04; A61H 2230/04; A61H 2230/045; A61H 2230/25; A61H 2230/255; A61H 2230/30; A61H 2230/305; A61H 2201/1609; A61H 2201/1611; A61H 2201/50; A61H 2201/5007; A61H 2201/5056; A61H 2201/5058; A61H 2201/5071; A61H 2201/5079; A61H 2201/5087; A61H 2201/5092; A61B 5/0053; A61B 5/02007; A61B 5/02035; A61B 5/02141; A61B 5/021; A61B 5/022; A61B 5/026; A61B 5/4836; A61B 5/6822; A61B 5/6831; A61B 8/06; A61B 8/42; A61B 8/4227; A61B 8/4477; A61B 8/488; A61B 17/135; A61B 17/1355

See application file for complete search history.

(56) References Cited

U.S. PATENT DOCUMENTS

| | | | |
|---|---|---|---|
| 2,676,586 A | 4/1954 | Coakwell, Jr. | |
| 3,587,584 A | 6/1971 | Bourbon | |
| 4,676,232 A | 6/1987 | Olsson et al. | |
| 4,686,085 A | 8/1987 | Osterholm | |
| 4,745,924 A | 5/1988 | Ruff | |
| 5,234,459 A | 8/1993 | Lee | |
| 5,271,409 A | 12/1993 | Millay | |
| 5,312,350 A | 5/1994 | Jacobs | |
| 5,348,015 A | 9/1994 | Moehring | |
| 5,372,575 A | 12/1994 | Sebastian | |
| 5,376,067 A | 12/1994 | Daneshvar | |
| 5,441,051 A | 8/1995 | Hileman | |
| 5,514,079 A | 5/1996 | Dillon | |
| 5,685,321 A | 11/1997 | Klingenstein | |
| 5,741,295 A | 4/1998 | McEwen | |
| 5,792,173 A | 8/1998 | Breen | |
| 6,063,036 A | 5/2000 | Li | |
| 6,238,413 B1 | 5/2001 | Wexler | |
| 6,299,629 B1 | 10/2001 | Gruenfeld | |
| 6,336,901 B1 | 1/2002 | Itonaga et al. | |
| 6,547,736 B1 | 4/2003 | Moehring | |
| 7,074,177 B2 | 7/2006 | Pickett | |
| 7,314,478 B2 | 1/2008 | Hui | |
| 7,727,254 B2 | 6/2010 | Pah | |
| 7,972,356 B2 | 7/2011 | Boyle et al. | |
| D643,536 S | 8/2011 | Vivenzio | |
| 7,988,104 B1 | 8/2011 | Cook et al. | |
| 7,998,104 B2 | 8/2011 | Chang | |
| 8,025,674 B2 | 9/2011 | Barbut et al. | |
| 8,062,324 B2 | 11/2011 | Shimon et al. | |
| 2001/0025643 A1 | 10/2001 | Foley | |
| 2003/0167070 A1 | 9/2003 | McEwen | |
| 2004/0098035 A1 | 5/2004 | Wada | |
| 2005/0075531 A1 | 4/2005 | Loeb et al. | |
| 2006/0058840 A1 | 3/2006 | Payne | |
| 2006/0100530 A1 | 5/2006 | Kliot | |
| 2006/0241485 A1 | 10/2006 | Hacker | |
| 2007/0161933 A1 | 7/2007 | Ravikumar | |
| 2007/0173886 A1 | 7/2007 | Rousso | |
| 2007/0191881 A1 | 8/2007 | Amisar | |
| 2008/0154140 A1 | 6/2008 | Chang et al. | |
| 2008/0262535 A1 | 10/2008 | Gavriely et al. | |
| 2008/0312562 A1* | 12/2008 | Routh | A61N 7/02 601/2 |
| 2009/0099447 A1* | 4/2009 | De Korte | A61B 5/02007 600/438 |
| 2009/0209925 A1 | 8/2009 | Marinello | |
| 2009/0287101 A1 | 11/2009 | Ferren | |
| 2010/0082060 A1 | 4/2010 | Avitable | |
| 2010/0094332 A1 | 4/2010 | Willshaw | |
| 2010/0324429 A1 | 12/2010 | Leschinsky | |
| 2010/0324589 A1 | 12/2010 | Carpenter et al. | |
| 2011/0028934 A1 | 2/2011 | Buckman et al. | |
| 2011/0054322 A1* | 3/2011 | Zanatta | A61B 5/02007 600/443 |
| 2011/0251635 A1 | 10/2011 | Caldarone | |
| 2012/0035652 A1 | 2/2012 | McGrimley | |
| 2012/0150215 A1 | 6/2012 | Donald | |
| 2012/0232578 A1 | 9/2012 | Altobelli | |
| 2013/0023909 A1 | 1/2013 | Duhay | |
| 2013/0150733 A1* | 6/2013 | Solomon | A61B 5/0059 600/479 |
| 2013/0304111 A1 | 11/2013 | Zhadkevich | |
| 2014/0081098 A1* | 3/2014 | Cohrs | A61B 5/029 600/324 |
| 2014/0135816 A1 | 5/2014 | Hyde et al. | |
| 2014/0194740 A1* | 7/2014 | Stein | A61B 8/085 600/455 |
| 2014/0236221 A1 | 8/2014 | Zhadkevich | |
| 2014/0277101 A1 | 9/2014 | Smith | |
| 2014/0371593 A1* | 12/2014 | Kondoh | A61B 8/5223 600/443 |
| 2015/0018869 A1 | 1/2015 | Benz et al. | |
| 2015/0080942 A1 | 3/2015 | Garrison | |
| 2015/0313607 A1 | 11/2015 | Zhadkevich | |
| 2016/0030001 A1 | 2/2016 | Stein | |
| 2016/0317370 A1* | 11/2016 | Evans | A61G 7/05776 |

FOREIGN PATENT DOCUMENTS

| | | |
|---|---|---|
| EP | 0203310 A2 | 12/1986 |
| EP | 0 462 088 A2 | 12/1991 |
| EP | 0934726 A1 | 8/1999 |
| EP | 2662034 A1 | 11/2013 |
| EP | 2796099 A1 | 10/2014 |
| FR | 699349 A | 2/1931 |
| FR | 719730 A | 2/1932 |
| WO | WO 98/46144 A1 | 10/1998 |
| WO | WO 99/36028 A1 | 7/1999 |
| WO | WO 2007/074350 A1 | 7/2007 |
| WO | WO 2008/009932 A1 | 1/2008 |
| WO | WO 2008/150966 A1 | 12/2008 |
| WO | WO 2010/141752 A1 | 12/2010 |
| WO | WO 2011/088543 A1 | 7/2011 |
| WO | WO 2014/027347 A1 | 2/2014 |
| WO | WO 2014/037960 A1 | 3/2014 |
| WO | WO 2014/070993 A1 | 5/2014 |

OTHER PUBLICATIONS

Gabor Erdoes, MD, titled "Letter by Erdoes et al Regarding Article, 'Cerebral Embolization During Transcatheter Aortic Valve Implantation: A Transcranial Doppler Study," item title "Journal of the American Heart Association"; copyright 2013; p. 590; No. 127;

(56) References Cited

OTHER PUBLICATIONS

American Heart Association, Inc.; Dallas Texas, USA; copy enclosed (2 pages).

Marie-Christine Guilbert, titled "Arterial trauma during central venous catheter insertion: Case series, review and proposed algorithm," item title "Journal of Vascular Surgery", copyright 2008, pp. 918-925, vol. 48, No. 4, Canadian Society for Vascular Surgery; Montreal, Quebec, Canada; copy enclosed (8 pages).

Philipp Kahlert, "Cerebral Embolization During Transcatheter Aortic Valve Implantation: A Transcranial Doppler Study," Item titled "Journal of the American Heart Association", copyright Aug. 16, 2012; pp. 1245-1255; No. 126; American Heart Association, Inc.; Dallas, Texas, USA; copy enclosed (16 pages).

H. Loffler; Stratum corneum adhesive tape stripping: influence of anatomical site, application pressure, duration and removal; British Journal of Dermatology; 2004; pp. 746-752; vol. 151; publisher United States Patent and Trademark Office; Published United Kingdom; copyright 2004 British Association of Dermatologists; copy enclosed (8 pages).

European Patent Office; Extended European Search Report; European Application No. 16191238.1-1666; European Patent Office; pp. 1-6; publisher European Patent Office; Published Munich Germany; copyright and dated Feb. 2, 2017; copy enclosed (6 pages).

European Patent Office; Communication Regarding Extended European Search Report pursuant to Rule 62 EPC; European Application No. 17190479.0-1122; European Patent Office; pp. 1-7; publisher European Patent Office; Published Munich Germany; copyright and dated Jan. 16, 2018; copy enclosed (7 pages).

European Patent Office; Communication Regarding Extended European Search Report pursuant to Rule 62 EPC; European Application No. 17199143.3-1122; European Patent Office; pp. 1-10; publisher European Patent Office; Published Munich Germany; copyright and dated Feb. 14, 2018; copy enclosed (10 pages).

* cited by examiner

DEVICE AND METHOD FOR SIMULTANEOUS DETECTION, MONITORING AND PREVENTION OF CEREBRAL EMBOLI

CROSS REFERENCE TO RELATED APPLICATION

The present application claims benefit to U.S. Patent Application No. 62/233,445 filed on Sep. 28, 2015 and entitled, "Device and Method for Simultaneous Detection, Monitoring and Prevention of Cerebral Emboli", the contents of which are incorporated by reference in their entirety herein for all purposes.

FIELD OF INVENTION

The present invention relates to a device and method for detecting and preventing cerebral emboli and stroke as a consequence of "emboligenic" interventions, such as procedures on the heart, heart valves, coronary arteries and aorta. More particularly, the present application involves a non-invasive apparatus, applied to the neck of the patient, that provides automated anatomic localization of the artery carrying blood to the brain (such as the carotid or vertebral artery), self-positioning and monitoring of the arterial flow through the artery, and detection of cerebral emboli and prevention of their influx to the brain by virtue of intermittent timed compression of the arteries carrying the emboli to the brain. An automated diagnostic and therapeutic feedback system and a method of use are also provided.

BACKGROUND

Intraoperative embolic stroke is one of the most tragic complications of cardiac, aortic and vascular procedures, found by MRI in up to 84% of patients depending on the type of the procedure. These embolic events are caused by cerebral emboli and lead to patients' cognitive impairment, disability, prolonged recovery and increased mortality. The main sources of cerebral emboli and stroke in this setting reside in the heart, heart valves, thoracic aorta, and great vessels when these structures are intervened thereon. Even simple cardiac catheterization with an endovascular catheter can induce microtrauma of the atherosclerotic thoracic aorta leading to the formation of embolic particles with subsequent embolic brain injury ranging from latent ischemic foci to a massive or even fatal stroke.

Multiple devices are known that attempt to detect and monitor cerebral emboli such as transcranial Doppler ultrasound (TCD), transthoracic echocardiography (TTE), transesophageal echocardiography (TEE), etc. Such devices, however, have significant shortcomings that do not allow for a reliable detection of cerebral emboli and do not address the problem of their prevention at the time of their detection. For example, a transcranial Doppler device (TCD) has been used for continuous detection and monitoring of cerebral emboli, however, even if cerebral emboli are detected, the TCD and other ultrasound devices do not provide any features that allow for the prevention of such emboli from further propagation into cerebral vessels causing a stroke. Unfortunately, TCD devices are able to detect the emboli only when they have already reached the brain, i.e. too late, when nothing can be done to stop the emboli from inducing embolic stroke. The quality of the transcranial Doppler signal is significantly distorted by the human skull, requiring use of a low frequency insonation (1.5-2 MHz) and very limited acoustic windows that are very difficult to obtain. Moreover, known TCD and other devices are very hard to use in the setting of the operating room or an endovascular suite, as they occupy a lot of space, require a special head frame or a headset placed on the patient's head, are hard to position and are not able to reliably maintain their position over the patient's arteries during the whole period of time while the surgical procedure is performed. The application, positioning, and use of such devices require the involvement of specifically trained personnel. This increases the number of people in the operating room and clutters the area around the patient. The safety of TEE and a TCD, especially when a long term insonation of the brain is performed, is still a major concern and should be seriously considered. Most importantly, such devices are purely diagnostic and are unable to provide any immediate preventive measures on the basis of the information obtained.

Multiple other devices are known that attempt to prevent embolization of the carotid and other cerebral arteries during endovascular and cardiac interventions by using different types of filters, deflection devices or endoluminal balloons. These anti-embolic devices, however, create additional risk due to their complexity and invasive character with the further trauma to the inner vessel wall, generating additional cerebral emboli and resulting in a high risk to benefit ratio. Known devices require insertion of additional hardware into the arterial system or aorta, a procedure that is known by itself to be associated with all classical risks of endovascular intervention, including aortic dissection, bleeding, thrombosis, cerebral embolization and stroke. One known intra-aortic filter device that is inserted into the ascending portion of the thoracic aorta via an aortic cannula to capture potential embolic material released from the heart and aortic wall during heart surgery was found to be quite difficult to implement and was reported to be associated with major trauma to the aortic wall and acute aortic dissection.

Aside from introducing hardware into the patient and causing the aforementioned problems, intravascular filters are not able to simultaneously detect cerebral emboli and promptly notify the health care provider about the embolic event while immediately initiating the measures to protect the brain. Moreover, their use involves a long, continuous process of straining the blood flowing to the brain. This process takes hours and lasts throughout the whole course of the surgical procedure, in spite of the fact that the embolic showers that cause a stroke are very short with the majority of emboli disappearing from the arterial system within the first 30-60 seconds of each emboligenic event. Furthermore, placement of a filter on the way of the blood flowing to the brain invariably limits the flow going through and is invariably associated with deceleration of the cerebral flow, which is especially dangerous when a condition of a slow flow to the brain is maintained for a long time. In order to decrease the degree of limitation of the cerebral flow by the intravascular filter, some authors resort to increasing the size of pores of filters to allow for more blood flowing therethrough while capturing or deflecting only the emboli of a bigger size. This measure, however, increases the risk of cerebral embolization by particles smaller than the size of the filter pores (usually between 140 and 240 microns), whereas the majority of emboli are known to be less than 100 microns in size. Furthermore, the placement of the filter by itself may produce cerebral emboli. For example, the mere passing of a guide wire into a carotid artery generates approximately 40,000 microemboli, with a significant percentage of small, less than 60 microns, particles that are not retained by standard filters.

Therefore, in spite of multiple innovations in the field of detection and prevention of cerebral emboli, the problem of simultaneous detection and prevention of cerebral emboli and stroke during cardiovascular and other medical interventions is far from being resolved. At the present time there is no device that is able to provide both diagnosis (detection) and simultaneous treatment (prevention) of cerebral emboli. As such, there remains room for variation, significant improvement and innovation within the art.

BRIEF DESCRIPTION OF DRAWINGS

A full and enabling disclosure of the present invention, including the best mode thereof, directed to one of ordinary skill in the art, is set forth more particularly in the remainder of the specification, which makes reference to the appended Figs. in which:

FIG. 16-B is a partial cross-sectional view of a compression member that carries three vascular probes in which each probe is located at a different position relative to an area of compression and wherein the angle of insonation is adjustable depending on the degree of the inflation of a compression member.

Figure 1:
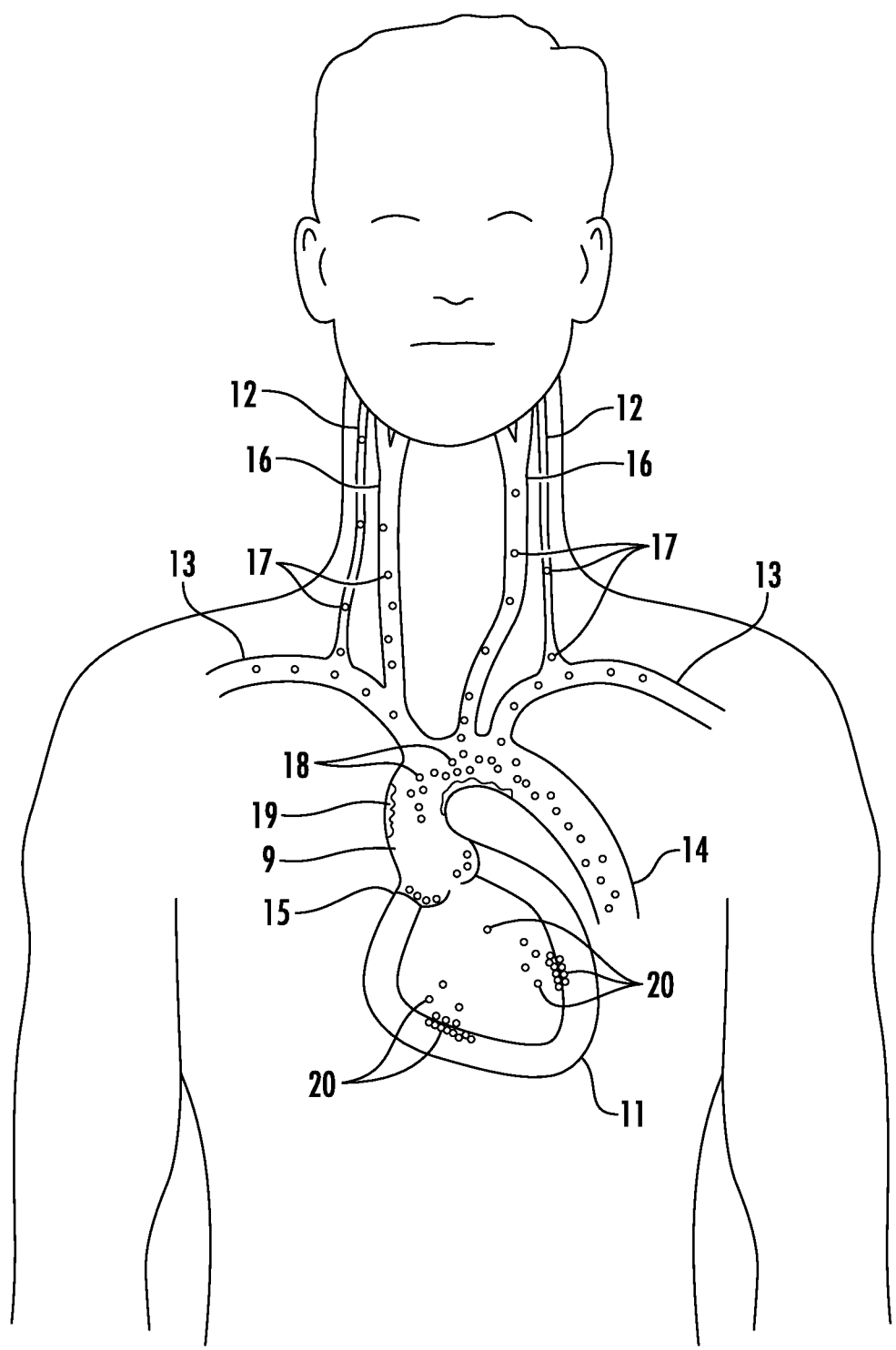
FIG. 1 is a front view of a patient with emboli in the heart and thoracic aorta with subsequent propagation of emboli into both carotid and vertebral arteries with the source of emboli being diseased aorta, aortic valve and the heart.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an apparatus and method of both detecting and preventing cerebral emboli and embolic stroke by controlled compression of the neck arteries such as carotid and/or vertebral arteries based on the data obtained via the vascular probes incorporated into the compression mechanism, and synchronized with the appearance of emboli in the circulatory system.

A device 26 is placed around the neck of a patient and can include a compression member 27 and a compression member 46 positioned along the long axis of the neck artery and/or a compression member 32 positioned across the long axis of the neck artery. The members 27, 46 and 32 comprise vascular probes 62, 64, 66, 68, 82, 84 such as an ultrasound probe, a flow probe, an oximeter probe, a pulse probe or any other vascular probe on their surface facing the area of the neck arteries (FIGS. 3-7). The members 27, 32, 46 may have different shapes such an oval shape (FIG. 8B), conal shape (FIG. 8C), pear shape (FIG. 10), crescent or complex multicomponent shape (FIG. 11), and/or finger shape (FIG. 12) facilitating and optimizing the process of their self-positioning in the vascular groove of the neck between the trachea 34 and the neck muscles 36 comprising the sternocleidomastoid muscle, scalene muscles, longus colli muscles and omohyoid muscles urging the vascular probe/probes 62, 64 and/or 66, 68, 82, 84 against the neck artery such as the carotid artery 16 and/or vertebral artery 12 upon actuation. When actuated such compression members 27, 46, 32 will press the vascular probes 62, 64 and/or 66, 68, 82, 84 against the neck arteries 12, 16 leading to contact with and compression of the arteries 12, 16 and monitoring of the anatomical and physiological parameters of the artery 12, 16, such as blood velocity, blood flow, diameter of the artery, the anatomical extent of compression, embolic signals, frequencies, angles and depths of insonation (analogous to High Intensity Transient Signals or HITS, obtained by Transcranial Doppler ultrasound), as well as pulse signals, oximetry signals and others.

The members 27, 46 and 32 can be expanded from an unactuated state to an actuated state in which the members 27, 46 (and in some embodiments—member 32) enter the vascular groove between the trachea 34 and the neck muscles 36, comprising the sternocleidomastoid muscle, scalene muscles, longus colli muscles and omohyoid muscles, urging the vascular probes 62, 64 and/or 66, 68, 82, 84 to create areas of controlled compression 23 at the carotid arteries 16 and/or vertebral arteries 12 to limit blood flow therethrough into the cerebral circulation. As a result, a pressure gradient is created in the proximal segments of the neck arteries 16 and/or 12 leading to diversion of the emboli 17, 18 (FIGS. 1-2) that are formed in the patient secondary to emboligenic intervention away from the arteries 12, 16 and preventing the patient from having an embolic stroke. Emboli 17 and 18 are diverted into a descending aorta 14, subclavian artery 13 and other vascular structures. The degree of compression is assessed and controlled on the basis of information received from the vascular probes 62, 64 and/or 66, 68, 82, 84 located at the area of compression of the arteries 12, 16. Such information can comprise blood velocity, a scanned image of the arteries 12, 16, changes in dimensions of the arteries 12, 16, detection of embolic particles, assessment of the regional and systemic arterial pressures and intraluminal pressures inside the compression bladders, the degree and the extent of compression along and across the artery, pulse and oximetry signals, etc. The position of the probes 62, 64, 66, 68, 82, 84 in relation to the arteries 12, 16 and to the area of compression 23 (FIGS. 2B and 3A) may vary in such a way that in some embodiments one probe can occupy a position right at the area of arterial compression 23 (such as probe 62, FIGS. 4 and 5), whereas the other probe may be positioned downstream from the area (probe 66, FIG. 5), and yet another probe may be positioned upstream from the area of compression (probe 68, FIG. 5). In addition, each of the probes 62, 64, 66, 68, 82, 84 may occupy an adjustable angle in relation to the neck artery 12, 16 with the adjustable depth of insonation and multiple frequencies to meet the demands of multifunctional imaging, comprising measurements of embolic signals, flow velocities, M-Mode and B-mode anatomic imaging.

Such positioning would assure obtaining information regarding arterial flow, degree of reduction of the arterial lumen and blood velocity, degree of prevention from emboli 17, 18, including the number of emboli 17, 18 flowing toward the brain, the number of emboli 17, 18 that were deflected versus the number of emboli 17, 18 that were allowed to pass through the area of compression, the intensity of the embolic load (the number of embolic signals per second), etc.

Figure 7A:
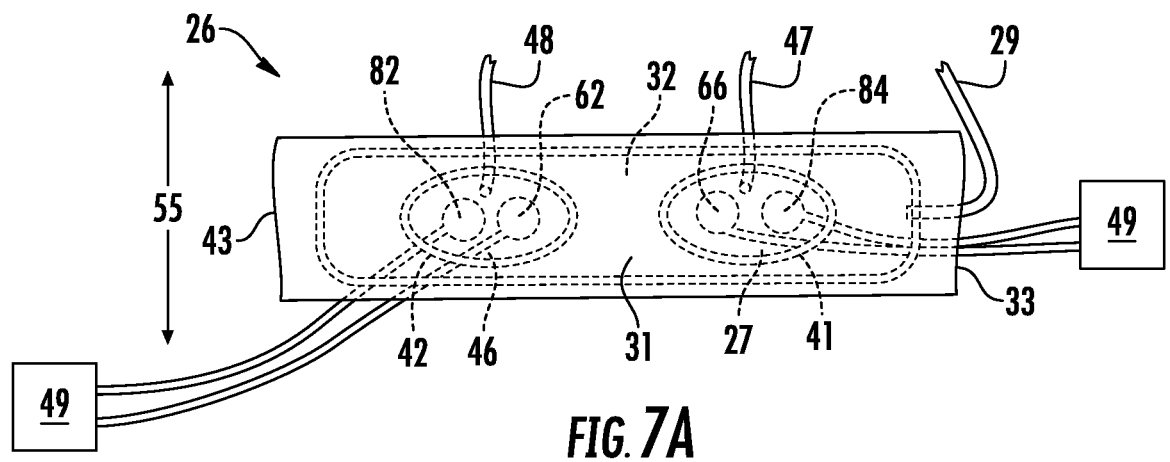
FIG. 7A is a front view of a device with monitoring vascular probes attached to the inner surface of the vascular compression members in accordance with another exemplary embodiment.
Figure 7B:
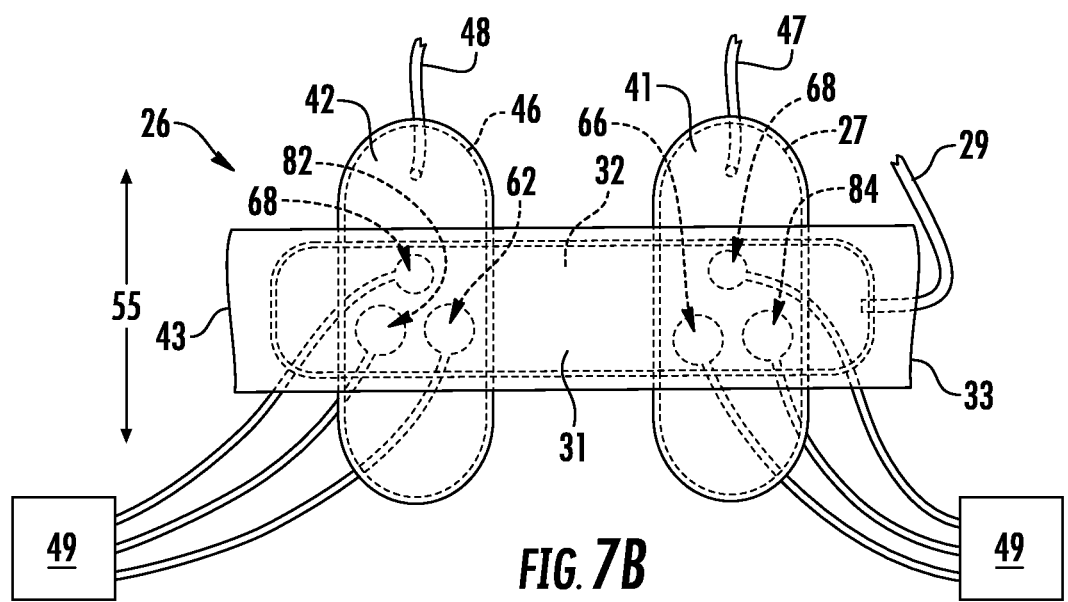
FIG. 7B is a front view of a device with monitoring vascular probes attached to the inner surface of the vascular compression members in accordance with another exemplary embodiment.

In other embodiments such positioning can comprise probes 82 and 84, located at the same level as probes 62, 64, 66 for simultaneous measurements of other, different vascular parameters at the same level of the compressed artery (FIG. 7A). In other embodiments however, such positioning may comprise additional probes 68 located slightly downstream from probes 62, 66, 82 and 84 (FIG. 7B). These parameters may be embolic signals detected with one probe (such as probe 62, 66 and/or 64, 68), and blood velocity, arterial diameter, or pulse oximetry or blood flow detected with other probes (such as probe 82, 84 and/or 68). The probes can be arranged so that one of the probes 66 measures a parameter of the artery 16, 12 that is an image of the artery 16, 12, and so that probe 68 measures a parameter that is the velocity of blood flowing through the artery 16, 12, and so that probe 84 measures a parameter of the artery 16, 12 that is emboli 17 present in the artery 16, 12. The three probes 66, 68, 84 that make these measurements may all be Doppler probes that work at different frequencies and that may be at different angles to the artery 16, 12.

Figure 9A:
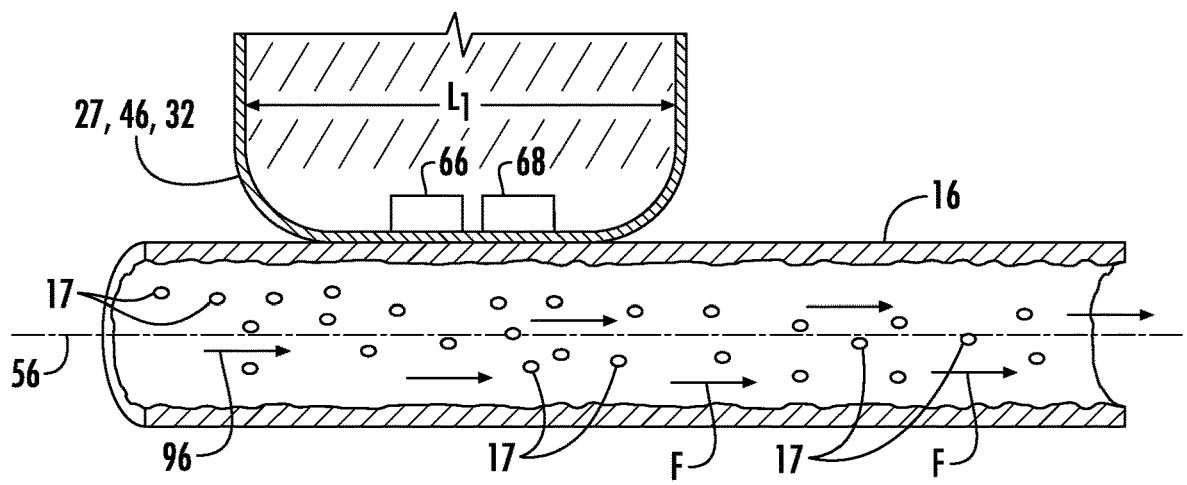
FIG. 9A is a cross-sectional view of the neck artery along its longitudinal axis with the compression member and vascular probes positioned against the artery.
Figure 9B:
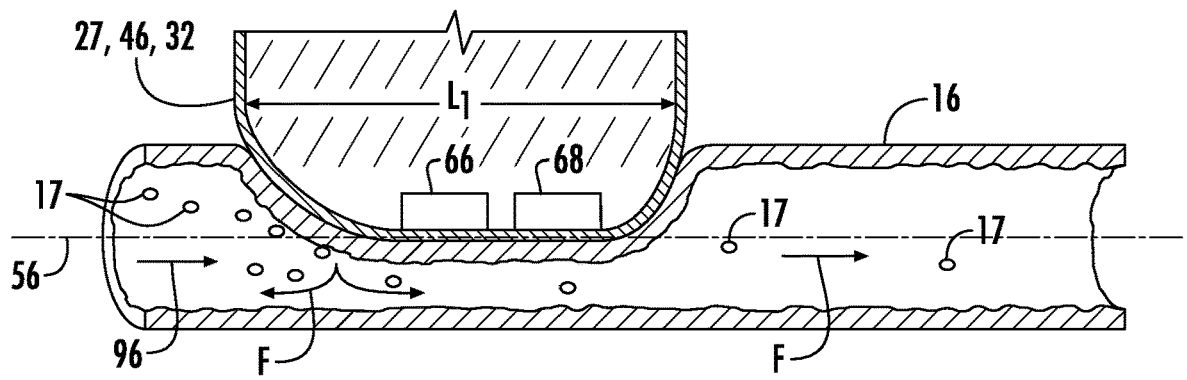
FIG. 9B is a cross-sectional view of the neck artery along its longitudinal axis with the compression member and vascular probes compressing the artery along the short distance L1.
Figure 9C:
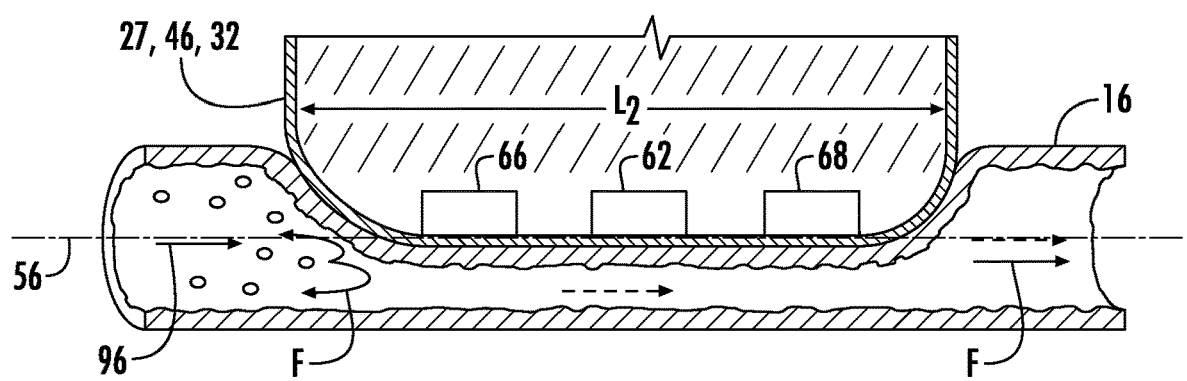
FIG. 9C is a cross-sectional view of the neck artery along its longitudinal axis with the compression member and vascular probes positioned compressing the artery along the long distance L2.

Another parameter influencing the degree of arterial compression and resistance to arterial flow is the length L (L1 or L2) along which the artery is compressed (FIGS. 9B and 9C). Depending on the design of the compression member the length L can be variable and extend, if necessary, from 1 to 5 cm, or more in other embodiments, in order to increase resistance to arterial flow and influx of emboli 17, 18. As depicted in FIGS. 9A, 9B and 9C, the compression member 27, carrying vascular probes 66, 68 and/or 62 that is in contact with the artery 16 may have a longitudinal dimension L1 (FIGS. 9A and B) that may be expanded to the dimension L2 (FIG. 9C) that would create a compression along the longitudinal axis 56 of the artery 16 (FIGS. 9B and 9C). This same length extension/control feature may apply for the compression members 46 and/or 32.

As shown on FIG. 9A the compression members 27, 46 or in some embodiments 32 carrying vascular probes 66, 68 are in contact with the neck artery 16. The emboli 17 are carried by the flow (shown with arrows F) towards the brain causing embolic stroke. The vascular probes, such as probes 66, 68, are able to detect physiological and anatomical parameters such as the diameter of the artery 16, blood velocity, the embolic signals, pulse oximetry waveform, etc. As there is no arterial compression (FIG. 9A), there is no resistance to the influx of emboli 17. However, as depicted in FIGS. 9B and 9C, once the artery 16 is compressed along the length L1 or L2, the dynamics of the flow and that of propagation of emboli 17 changes with less emboli 17 going through the artery 16 towards the brain. Moreover, if the artery is compressed along the distance L1 (FIG. 9B) that is significantly shorter than the distance of compression L2 (FIG. 9C), the degree of resistance to the arterial inflow 96 will be less with some of emboli 17 going through the artery 16 in spite of the artery 16 being compressed (FIG. 9B). However, in this case there will be more arterial flow still going to the brain than in the case depicted on FIG. 9C, where the artery 16 is compressed along a much longer distance L2. The emboli 17 can flow freely through the artery 16, 12 in FIG. 9A as there is no compression, and when some compression is exerted as shown for example in FIG. 9B less emboli 17 can be transferred past the point of compression and through the artery 16, 12. Further, when even more compression is applied such as in FIG. 9C even less emboli 17 than in FIG. 9B can be transferred or even no emboli 17 can be transferred through the artery 16, 12.

In some embodiments, the feedback mechanism between the vascular probes 66, 68, 62 will assure a lesser degree of compression when an embolic load detected by the vascular probes 66, 68, 62 is small, and a higher degree of compression when an embolic load is high. This goal will be achieved by either compressing the artery 16 to decrease its diameter (lumen), or by varying the length of the compression L with further elongation of the compression members 27, 46 and/or 32 from the length L1 to L2, if a higher degree of resistance to the influx of emboli 17 is desired. Thus, the distance L1 along which the neck artery 16 is compressed can be also variable and can be increased and changed to L2 when a more significant limitation of flow F to decrease the influx of cerebral emboli 17 is desired. This goal is achieved by increasing the length of the compression portion of the compression bladder 27, 46, 32 from L1 to L2, where L2 is significantly longer than L1 (FIG. 9). Such elongation of the compressing element can be achieved by increasing the pressure inside the compression bladder 27, 46, 32 with the bladder 27, 46, 32 made out of the material that would preferentially expand along the longitudinal axis 56 of the neck arteries 12, 16. In some embodiments the range of the length of compression L1 and L2 can vary between 1 and 5 cm along the course of the neck arteries, such as a carotid artery 16 and a vertebral artery 12. In this regard, L1 is 1 centimeter and L2 is 5 centimeters. In other embodiments, L1 is from 1-3 centimeters and L2 is from 4-6 centimeters.

With reference to FIG. 1 a front view of a patient is shown in which emboli 18 are transferred from the heart 11 into the aorta 9, carotid arteries 16 and vertebral arteries 12. Such emboli are shown in carotid arteries 16 and vertebral arteries 12 as emboli 17. The emboli 17 that are present in the carotid arteries 16 and vertebral arteries 12 can then be transferred into the cerebral circulation causing stroke of the patient. The emboli 18 and 17 may be fragments of atherosclerotic plaque of the aorta 19 that become dislodged during manipulation of the aorta 9. Also shown in FIG. 1 is calcification of the aortic valve 15 and intracardiac emboli 20 inside the chamber of the heart 11 that can also be the origin of emboli 17 eventually present in the carotid artery 16 and vertebral artery 12. The intracardiac emboli 20 may include air, gas, thrombi, microscopic parts of medical catheters, wires and atherosclerotic materials. Although all of the various emboli in the heart 11, aorta 9, 14 and aortic valve 15 need not be present in all instances, they are all shown in FIG. 1 for sake of example. Trauma to the heart 11, aortic valve 15, brachiocephalic (innominate) artery, aorta and other structures during placement and removal of items such as aortic clamps, balloons, catheters, guidewires and electrophysiological instruments, along with manipulations such coronary artery bypass grafting, aortic and mitral valve replacement, catheter ablation, endovascular grafting of the aorta 9, percutaneous implantation of the aortic or mitral valves, endovascular instrumentation of the aorta 9, aortic branches and the heart 11 may give rise to the presence of emboli 17 in the carotid arteries 16 and vertebral arteries 12. Critical moments of the aforementioned procedures (for example during the aortic cross clamp manipulation, aortic valvuloplasty or valve implantation, coronary interventions, and endovascular procedures on the aorta) may cause emboli 17 to form and cause stroke and are referred to as "emboligenic" events.

Figure 2A:
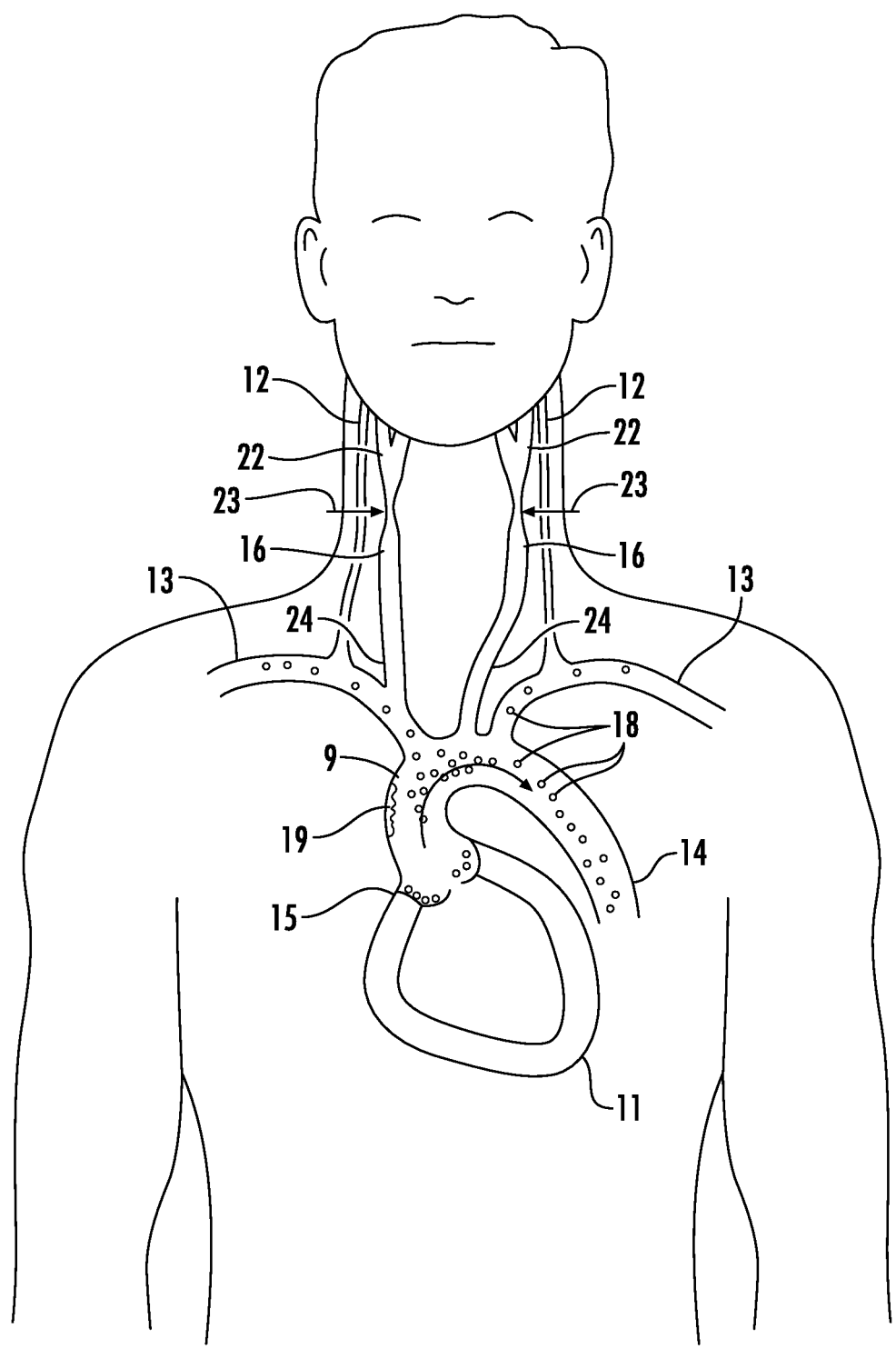
FIG. 2A is a front view of a patient with external compression of both carotid and vertebral arteries decreasing the blood inflow into these vessels and diverting emboli downstream.
Figure 2B:
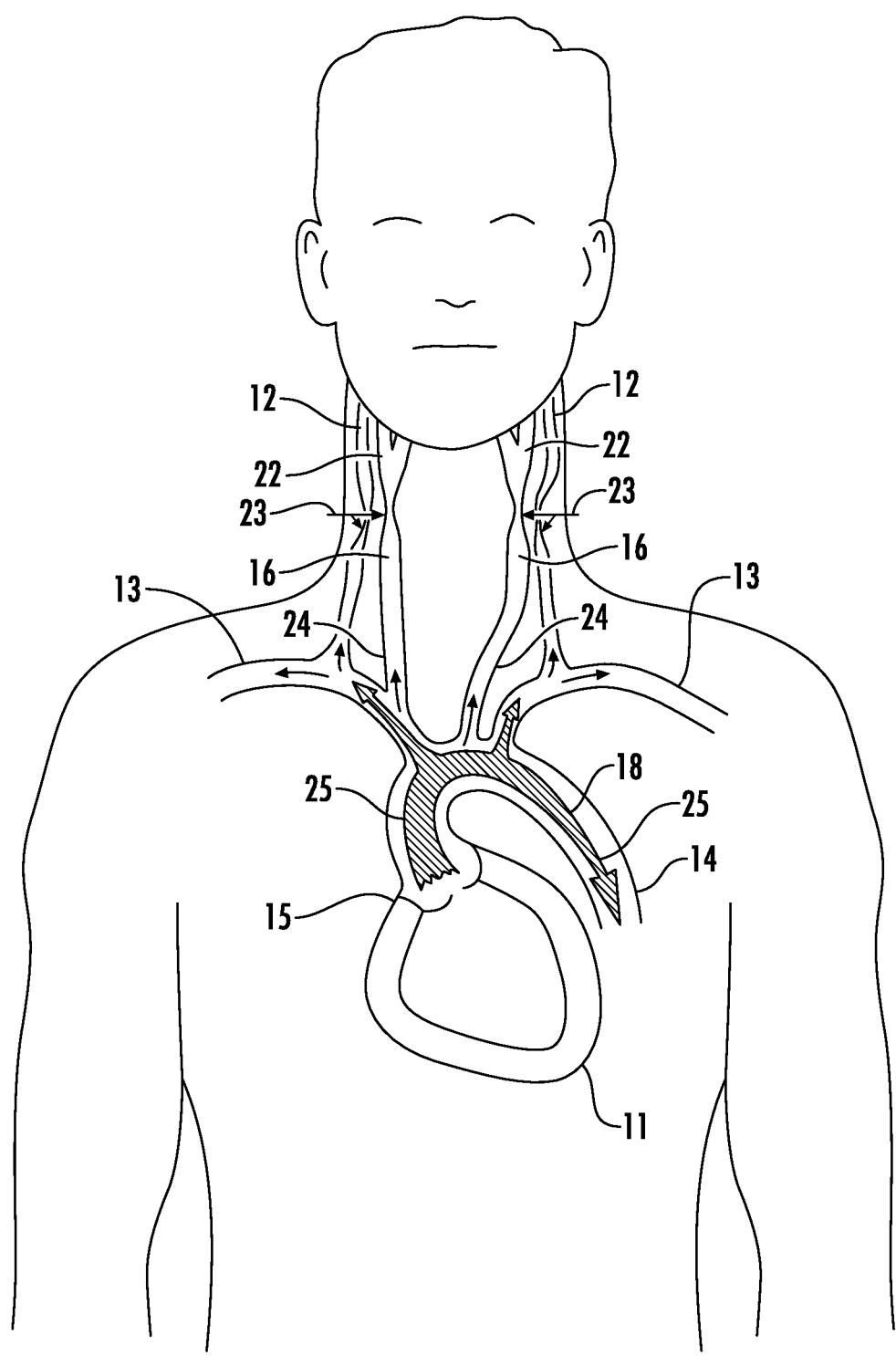
FIG. 2B is a front view of a patient with external compression that results in divergence of flow that carries emboli to the descending aorta and other vascular structures away from cerebral circulation.
Figure 3A:
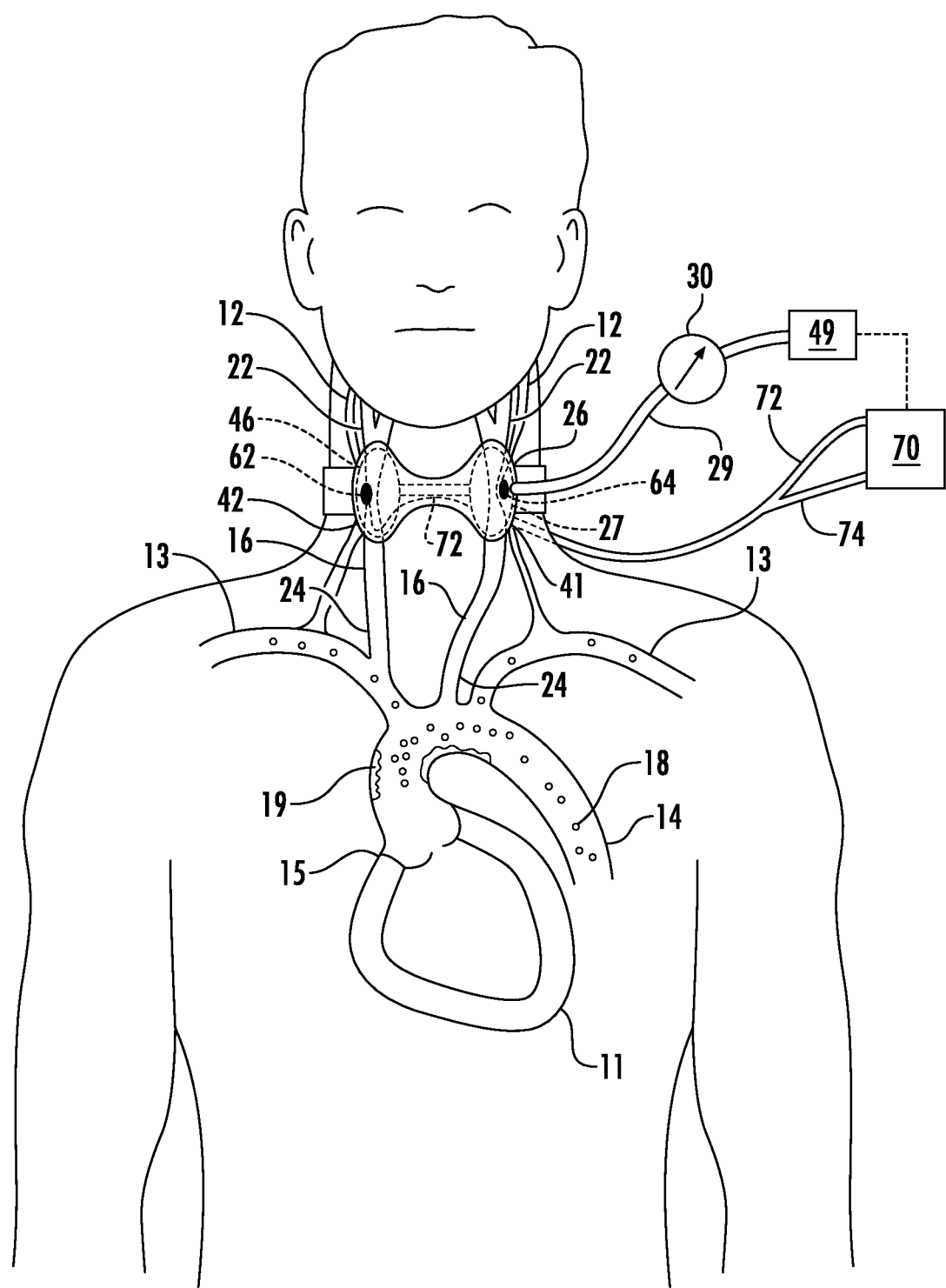
FIG. 3A is a front view of a patient with a device that is actuated in order to achieve an external compression and monitor the flow of blood and emboli through carotid and vertebral arteries.

FIGS. 2A, 2B and 3A show the disclosed method and the device for a controlled automated diverging of emboli 18 from cerebral circulation by exerting a controlled, and if necessary, automated, external compression to form areas of compression 23 at the carotid arteries 16 and vertebral arteries 12 to lead to temporary limitation or complete interruption of carotid and/or vertebral flow at the anticipated time intervals of impending cerebral embolization (emboligenic events). The distal carotid arteries 22 are present downstream from the areas of compression 23, and the proximal carotid arteries 24 are the portions of carotid arteries 16 upstream, that are farther from the brain, from the areas of compression 23. Upon creation of the areas of compression 23, a relative pressure gradient and a "low-flow" or a "no-flow" condition is produced in the proximal carotid arteries 24 that prevents emboli 18 from entering the cerebral circulation. A similar gradient is created in the proximal vertebral arteries upon their compression. In one embodiment these physiological and anatomical events are monitored and recorded by the vascular probes 62, 64 and/or 66, 68, 82 and 84 present at the compression apparatus and transmitted to the processor 70, providing a feedback mechanism for assuring a controlled operation of the compression system 49 that initiates actuation or de-actuation of the compression members 27, 46 and if needed 32.

The compression members 27, 46, 32 when actuated reach and compress the carotid 12 and/or vertebral 16 arteries. Such a feedback mechanism is designed to prevent the emboli 18 from entering the arteries 12, 16 (and produce a stroke) by providing compression of the neck arteries 12, 16 specifically at the time of the release and a washout of emboli 18 (usually less than 60-90 seconds) with a quick de-actuation of the compression members 27, 46, 32 and restoration of the cerebral perfusion as soon as the risk of embolism is gone. For example, the mere appearance of emboli 17 in the bloodstream of the arteries 16 and 12 is timely recorded by the vascular probes 62, 64 and/or 66, 68, 82 and 84. The probes 62, 64, 66, 82, 84 are incorporated into the compression members 27, 46, 32 that when actuated position themselves in the vascular groove of the neck assuring the position of vascular probes right against carotid 16 and/or vertebral 12 arteries. Such mechanism is then activated to compress the carotid 16 and/or vertebral 12 arteries to create a pressure gradient and to deflect the potential cerebral emboli 17 away from the brain. The detection of emboli 17 as well as determining the degree of compression of the arterial lumen, degree of alteration of the blood velocities, arterial flow and other parameters could be achieved by using different frequencies, angles and depths of an ultrasound, pulse oximetry and other techniques. In some embodiments, however, such an automated system and processor system 70 may be activated on demand by the health care provider in anticipation of embolic events, achieving the goal of presumptive protection of the cerebral circulation from upcoming emboli 17 that can be triggered by a specific command or a push of a button, activating the whole process of the controlled compression and release of the carotid 16 and/or vertebral 12 arteries. The proximal carotid arteries 24 are areas of the carotid arteries 16 upstream from the areas of compression 23 that have interrupted blood flow due to the compression. A similar gradient is achieved by compression of the vertebral arteries 12 and repetition of the steps discussed above is not necessary. As a result, potential carotid and vertebral emboli 17 are diverted into the descending aorta 14 and are illustrated as emboli 18. The arrow 25 shows preferential direction of the blood flow that carries potential cerebral emboli 17 into the descending aorta 14 when the areas of compression 23 are created. The disclosed method of a controlled diverging of the emboli 17 from the cerebral circulation comprises various degrees and combinations of compressing the lumen of the arteries 12, 16 by virtue of decreasing their cross-section (diameter) and the distance (length) of compression (distance L on FIG. 9) along the longitudinal axis of the arteries 12, 16 together with variations of the duration of the compression (optimally: from 20 to 90 seconds, or longer, if safe and necessary).

The degree of carotid compression as reflected by the changes of the diameter of the arteries 12, 16, the length of the compressed segment of the arteries 12, 16, the changes of the blood velocity, blood flow, changes in pulse signals, regional pressures and the amount of emboli 17 passing through is assessed and regulated on the basis of information received from the vascular probes 62, 64 and or 66, 68, 82 and 84 located on the surface of the compression members 27, 46, 32 and pressed against the neck arteries 12, 16. Coupling of these parameters with the arterial compression mechanism 49 responsible for actuating the compression members 27, 46, 32 will create an automated system for a controlled carotid 16 and/or vertebral 12 artery compression and prevention of cerebral emboli 17. As a result, a controlled, and in some instances an automated, compression of the neck arteries 12, 16 is achieved. Such compression is much safer as it is regulated on the basis of the information received from the vascular probes 62, 64, 66, 68, 82, 84 and can be regulated depending on the findings from them such as the presence of atherosclerotic plaque, appearance, time lag, direction and the number of embolic signals, degree of compression of the vascular lumen, extent of compression, changes in arterial blood velocity, risk of brain ischemia, etc. In addition, the assessment for authenticity of embolic signals (true embolus vs. an artifact) and their type (solid vs. fat vs. gas emboli) in these settings will be significantly improved due to a better chance for a multigated insonation, multiprobe and multidirectional insonation provided by the disclosed device. For example, a multiprobe insonation with the probe 64 located at the different segments of the artery 16 with the blood flow both flowing towards one probe 64 and away from the other probe 62, there will be a much better chance to discern the bidirectional embolic signals that are indicative of an artifact, but not of a true embolus. Moreover, the solid emboli 17, that are known to produce the most damaging cerebral insults, yet are the least discernible from the bloodstream due to their lower frequency, will be detected more reliably as compared to TCD due to significantly better backscattering at the level of the neck, where the skull interface is not present and when there are multiple probes 62, 64 to combine the results of multidirectional, multigated insonation creating a much better environment for detecting the low frequency and bidirectional embolic signals.

Figure 4:
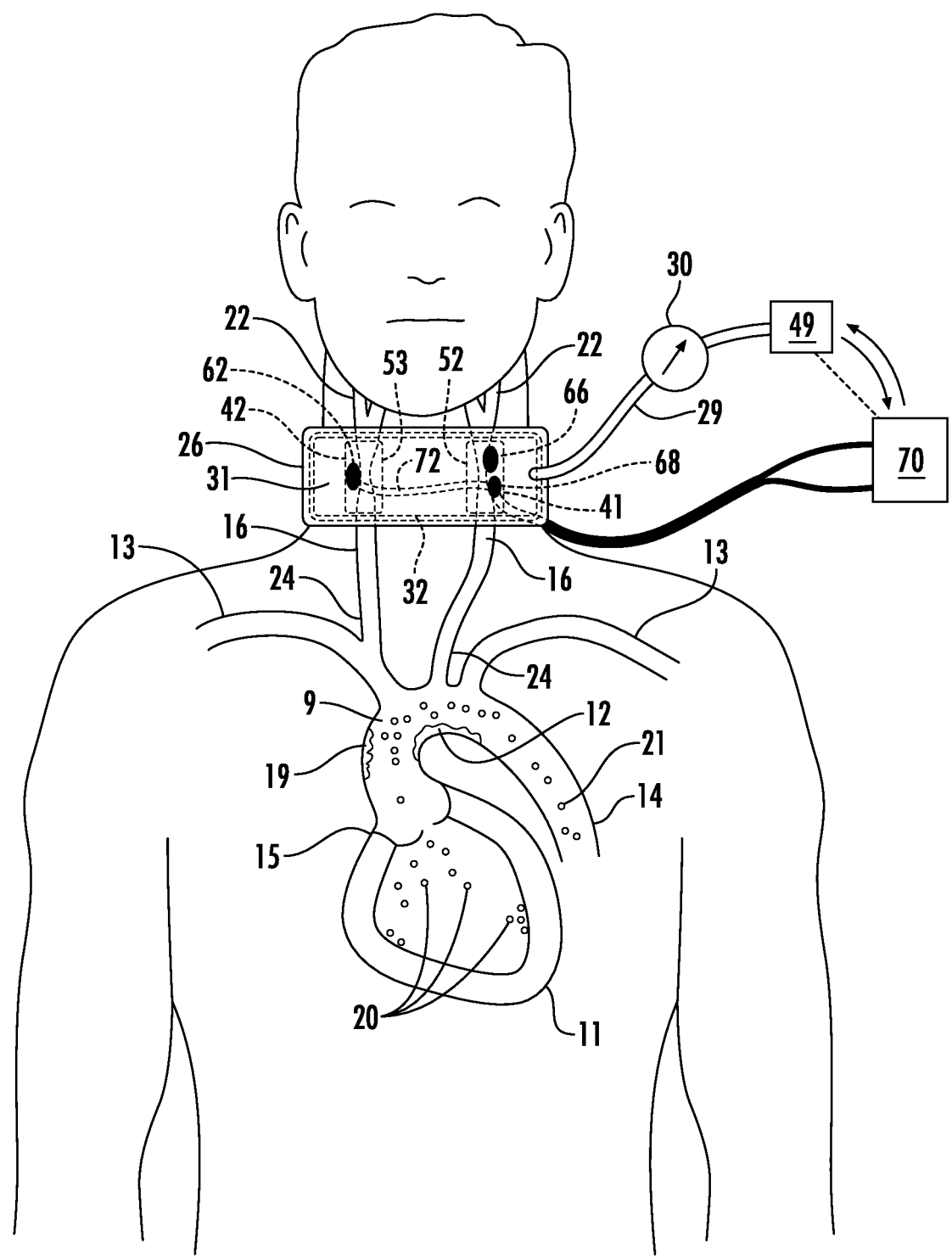
FIG. 4 is a front view of a patient with a device that features an option of using a transverse compression member and members of various shapes in accordance with other exemplary embodiments.
Figure 5:
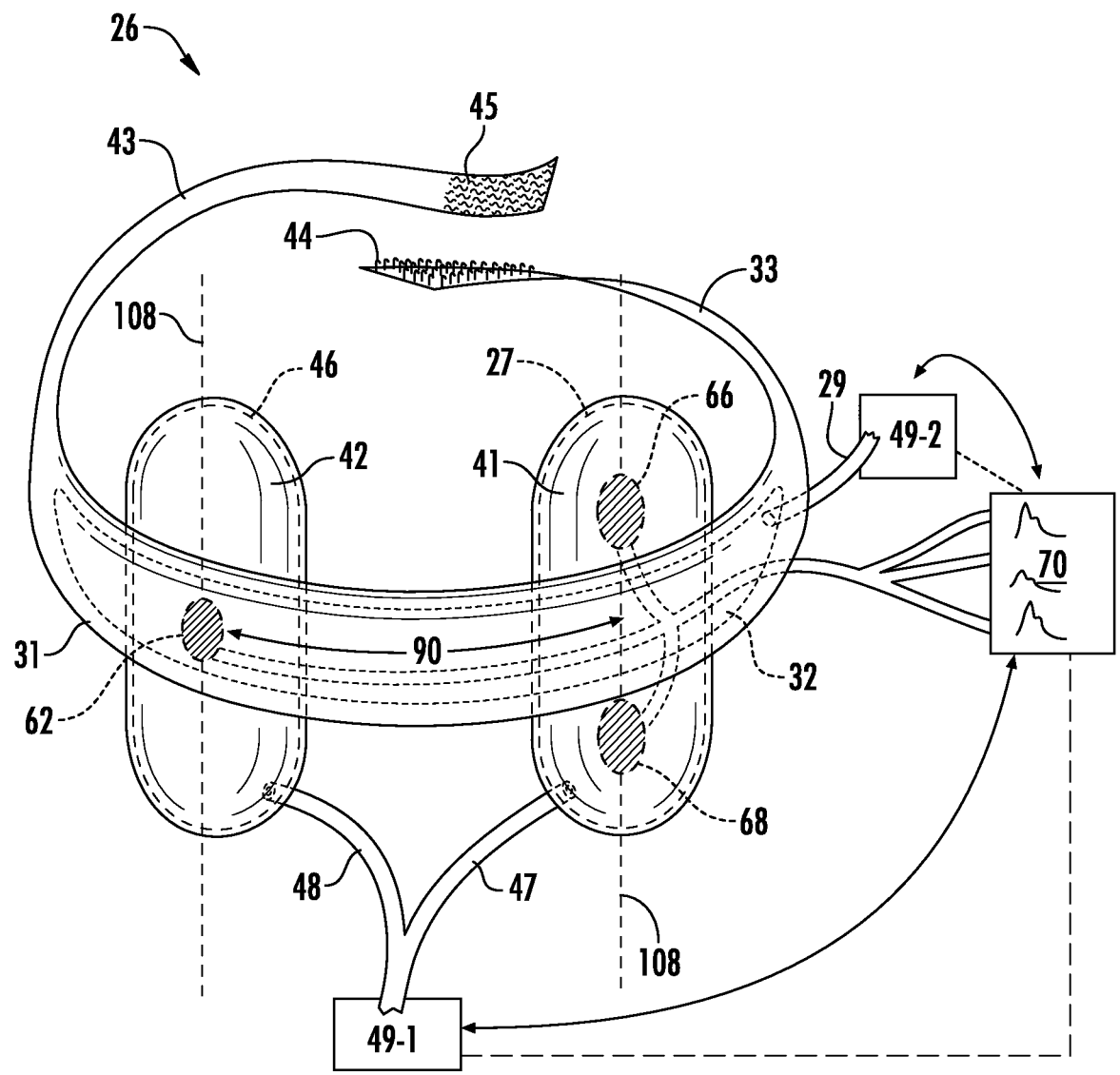
FIG. 5 is a perspective view of a device with monitoring vascular probes attached to the inner surface of the vascular compression members.

The feedback mechanism is provided by registering the anatomical and physiological parameters obtained by the vascular probes 62, 64, 66, 68, 82 and 84 from the artery with subsequent transfer of the data via the electric cords 72, 74 to the controlling device processor 70, where the information is processed and analyzed. The detection of certain physiological parameters such as the appearance, direction, time lag and the threshold number of embolic signals, changes of blood velocities, pulse signals, diameter and cross-sectional areas of the artery, blood flow, etc., will be processed in the processor unit 70 and will serve as a trigger to activate or deactivate the compression apparatus and a pressure source that is a component of the compression system 49 (FIGS. 3A, 4, 5). This regulates flow through the carotid arteries 16 and/or vertebral arteries 12, the degree and timing of the arterial compression and the need for its activation and release. This feedback mechanism will assure a safe and controlled interruption of the cerebral flow to deflect cerebral emboli 17 yet preserve an adequate blood supply to the brain tissue and avoid brain ischemia.

As depicted in FIGS. 3, 4, 5 and 6, an automated pressure source and compression mechanism 49 is included and is placed into fluid communication with a compression member 27 that is a first longitudinal carotid expandable member 27 by way of pressure tubing 29 that extends through a port of member 27. A pressure source of the compression system 49 is triggered by the processed information derived from the processor 70 providing for a real-time response to the changing characteristics of the carotid flow such an appearance of embolic signals. A manometer 30 may be included in the device 26 at some point between the member 27 and the automated pressure source 49 in order to monitor and measure pressure in the system. FIGS. 3C and 3D illustrate the device 26 once the pressure source 49 is activated in order to cause the device 26 to be pressurized. The pressure source 49 may be a pump that injects air, gas or liquid, such as water, through the pressure tubing 29. Injection of air or otherwise increasing the pressure causes the carotid compression member 27 to expand. Due to fluid communication through the connecting tube 54, the compression members 27, 46 may expand at the same rate to the same size. Expansion may be in the radial direction 57 towards the central longitudinal axis 56 of the neck artery 12, 16 such that the expandable members 27 and 46 expand towards axis 56 and away from the axis 56. In some exemplary embodiments, the members 27 and 46 may expand in the radial direction 57 towards the central longitudinal arterial axis 56 but not in the radial direction 57 away from the central axis 56. This arrangement may be accomplished by making portions of the expandable members 27 and 46, for example the portions facing away from the central axis 56 in the radial direction 57, such that they cannot expand while the portion facing towards the central axis 56 are in fact expandable. The expandable members 27 and 46 may be inflated to a pressure level that is just above the level of the patient's arterial pressure to achieve temporary interruption of the carotid blood flow. Both the left and right carotid arteries 16 and vertebral arteries 12 can be compressed at the same time, or separately.

FIGS. 3A-3D disclose an exemplary embodiment of a device 26 comprising compression members 27 and 46 where the shapes of such members and their anatomic position on the compression apparatus can be adjusted to promote an optimal regime of the carotid 16 and/or vertebral 12 arterial compression with the maximal effectiveness and minimal risk. In the optimal embodiment the distance 90 between the most central internal parts of members 27 and 46 (same as distance between the probes 62 and 64) corresponds to the distance between the areas of the carotid 16 and/or vertebral 12 arteries along the anterior neck curvature of a specific patient. This distance 90 may be the distance between centers 108 of the two compression member 27, 46 as measured along a curvature of the neck of the patient. Such distance can be measured directly on the patient's neck, or by using a computerized tomography and an ultrasound imaging. Next, on the basis of the anatomical neck assessment using the techniques a specific shape (FIGS. 8C, 10, 11, 12) of the compression member 27, 46, 32 is chosen that conforms most ideally to the space between the trachea 34 medially and the neck muscles 36 laterally in order to position the member 27, 46, 32 between these structures 34, 36 and thus to position the central (facing the patient) portion of the compression member 27, 46, 32 against the area of the carotid 16 and/or vertebral 12 artery on each side urging the vascular probes 62, 64, 66 or 68, 82, 84 against the arteries 12, 16 upon the actuation of the compression members 27, 46, 32.

Depending on the specifics of the neck anatomy in each case a different shape of the compression member 27, 46, 32 can be chosen, and such a member 27, 46, 32 can be placed into the holding pocket 41, 42 of the neck compression apparatus 26 (that can be in a form of a neck collar, a semicircle or a direct compressing arm) before its actuation. The holding pockets 41, 42 could include more rigid material than the balloons of the compression members 27, 46, 32 to cause them to assume a desired shape and size upon inflation. Such shape would assure a preferential expansion of the compression member 27, 46, 32 carrying the vascular probe towards the neck artery 16, 12 with the preferential orientation of the member 27, 46, 32 in the vascular groove between the trachea 34 and the neck muscles 36 right on top of the neck artery 16 and/or 12 with the direction of the compression forces in the radial direction 57 towards the central axis 56 of the neck arteries 16 12 urging the vascular probes 62, 64, 66, and/or 68, 82, 84 against the arteries 16, 12.

Depending on the patient's neck anatomy as estimated by the clinical exam comprising direct neck measurements and/or analyzing the data of the neck studies such as computerized tomography and ultrasound as indicated above, a choice of an optimal shape of the compression member 27, 46, 32 for each particular patient can be made. Such shape can be an oval shape (FIG. 8B), cone shape (FIG. 8C), pear shape (FIG. 10), crescent shape (FIG. 11), finger shape (FIG. 12) and/or any combinations of said shapes. The shapes are assumed by compression members 27, 46, 32 upon their actuation by virtue of a specific design of the compression member 27, 46, 32, where the specific shape is preformed before actuation, or achieved after actuation by virtue of different degrees of the compliance and expandability of the member's 27, 46, 32 material to internal pressurization leading to preferential expansion of the part of the member 27, 46, 32 facing the area(s) of the neck arteries 16 and/or 12 in the radial direction 57 (FIGS. 3B, 3C and 8A, 8B).

Figure 16A:
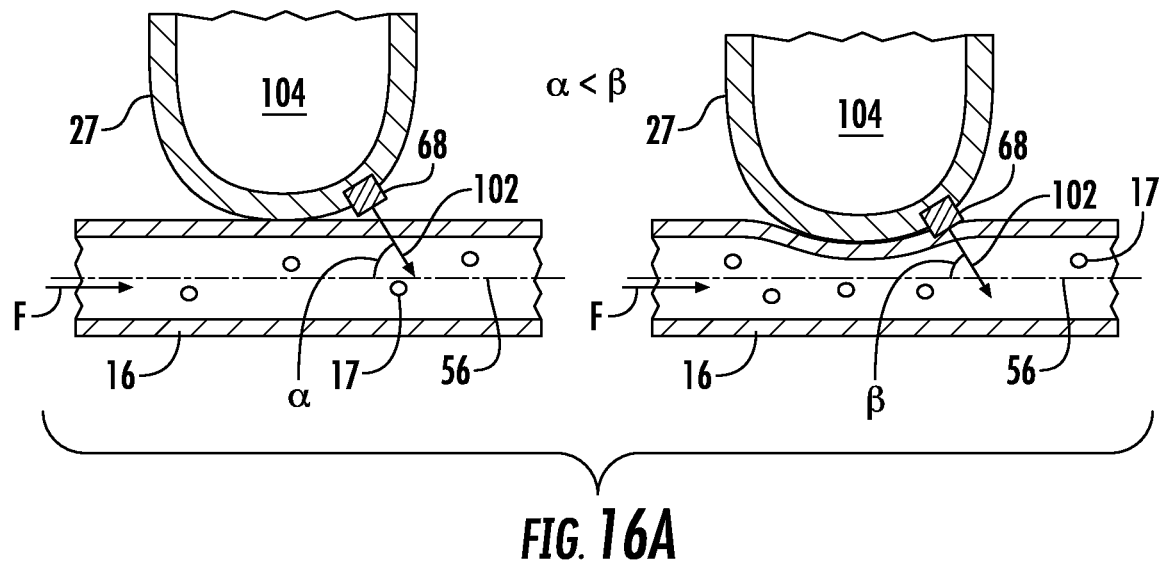
FIG. 16-A is a partial cross-sectional view of a compression member that carries one vascular probe in which the angle of a probe in relation to the underlying artery (angle of insonation) is adjustable by the inflation of the compression member.
Figure 16B:
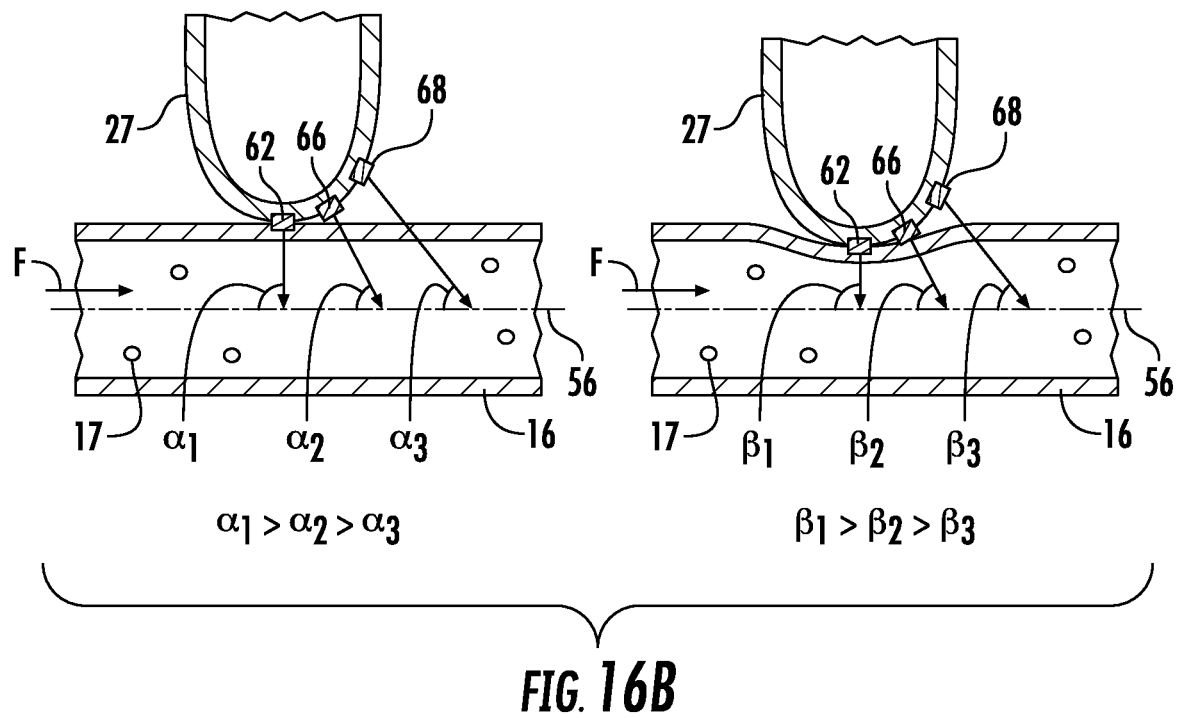

The preferential expansion occurs towards the central axis 56 of the arteries 16 and 12, and there may be only a limited or no expansion of the parts of the compression member 27, 46, 32 facing other areas such as the trachea 34 and neck muscles 36 or the area of an outward expansion in the direction opposite to the inward radial direction 57. The degree of expansion in these areas is less than the degree of expansion towards arteries 16, 12 by volume of the compression members 27, 46, 32. From this standpoint FIG. 3B may represent a device with the compression member 27, 46 of an oval shape or any other shape disclosed above before actuation. Upon actuation, by virtue of inflation or using any other way of pressurization, the member 27, 46 may assume an oval cross-sectional shape as shown in FIG. 3C with the preferential expansion inwards toward the neck artery 16 and/or 12 in the radial direction 57 with the vascular probes 62 and 64 moving centrally in the radial direction 57 towards the central longitudinal axis 56 of the artery 16 and/or 12. As depicted on FIG. 3D, the position of vascular probes 62, 66, 68 may be different, as they may occupy a central position on the compression bladder 27, 46 as the probe 62, or be positioned longitudinally along the long axis of the artery 16 as the probes 66 and 68. In other embodiments they can occupy positions perpendicular to the longitudinal axis of the arteries 16 and/or 12 as probes 62, 82 and 66, 84 in FIGS. 7A and 7B, or have a mixed arrangement with both longitudinal (probes 68) and transverse (probes 62, 82 and 66, 84) positioning in relation to the longitudinal axis of the arteries 16 as depicted in FIG. 7B. Such positioning, comprising a variable and adjustable angle of insonation (0-90%) in relation to the artery, variable depths (1-5 cm) and frequencies of insonation (1.5-8 MHz) would provide for multiple functions of the probes 62, 64, 66, 68, 82, 84 in terms of both information obtained (such as the real time imaging using the B- and M-mode, Duplex ultrasound, embolic count, the direction, velocity and the time lag of propagation of emboli 17, pulse oximetry, flowmetry, etc.) and the degree, the type and the angle of the carotid 16 and/or vertebral 12 compression for prevention of emboli. These results are achieved due to a disclosed feature of changing the geometry of the intersection between the ultrasound beam and the carotid 16 and/or vertebral 12 artery (FIGS. 16-A and 16-B).

Figure 8A:
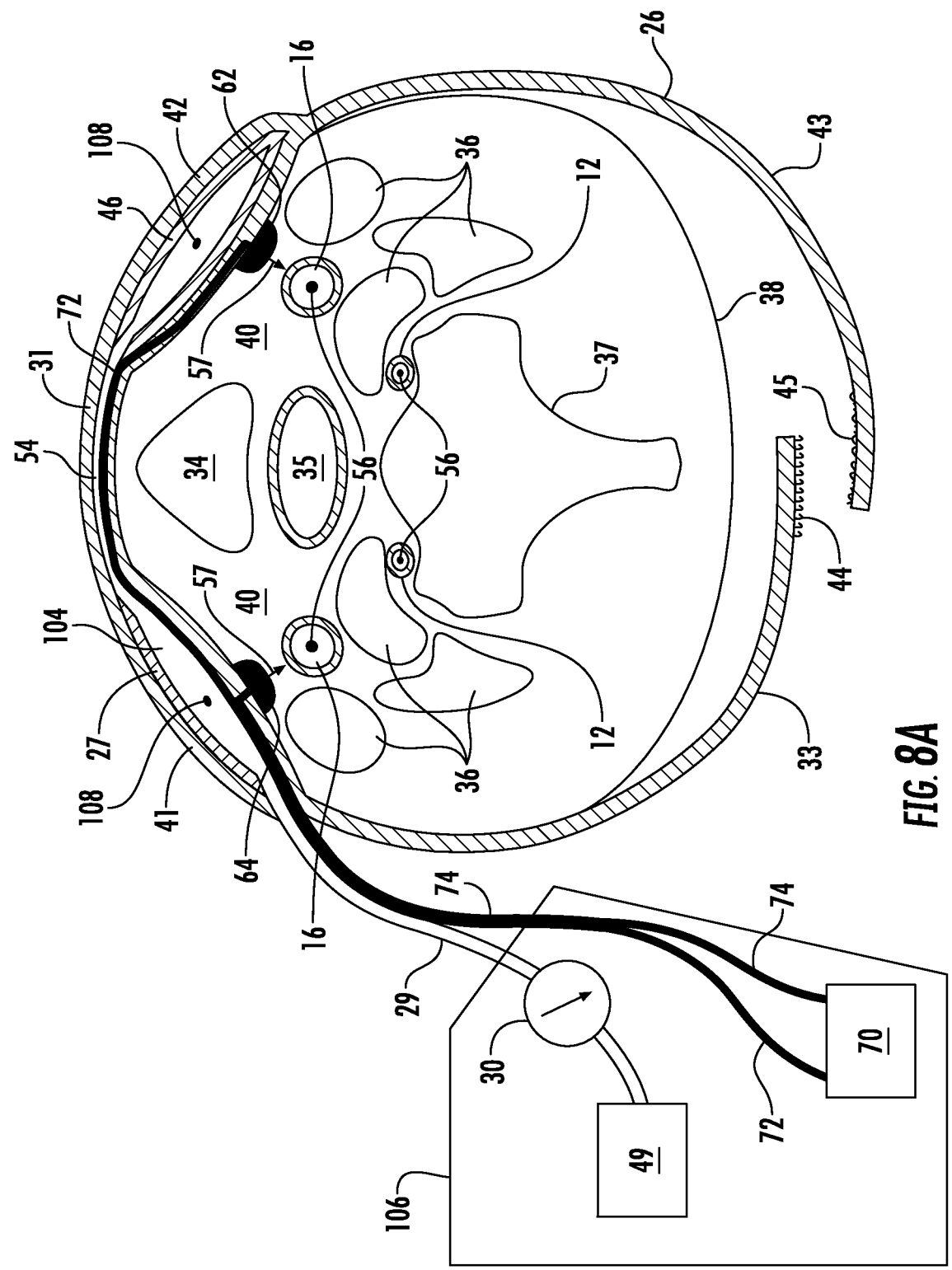
FIG. 8A is a cross-sectional view of a neck of a patient and a device attached thereto in an unactuated state.
Figure 8B:
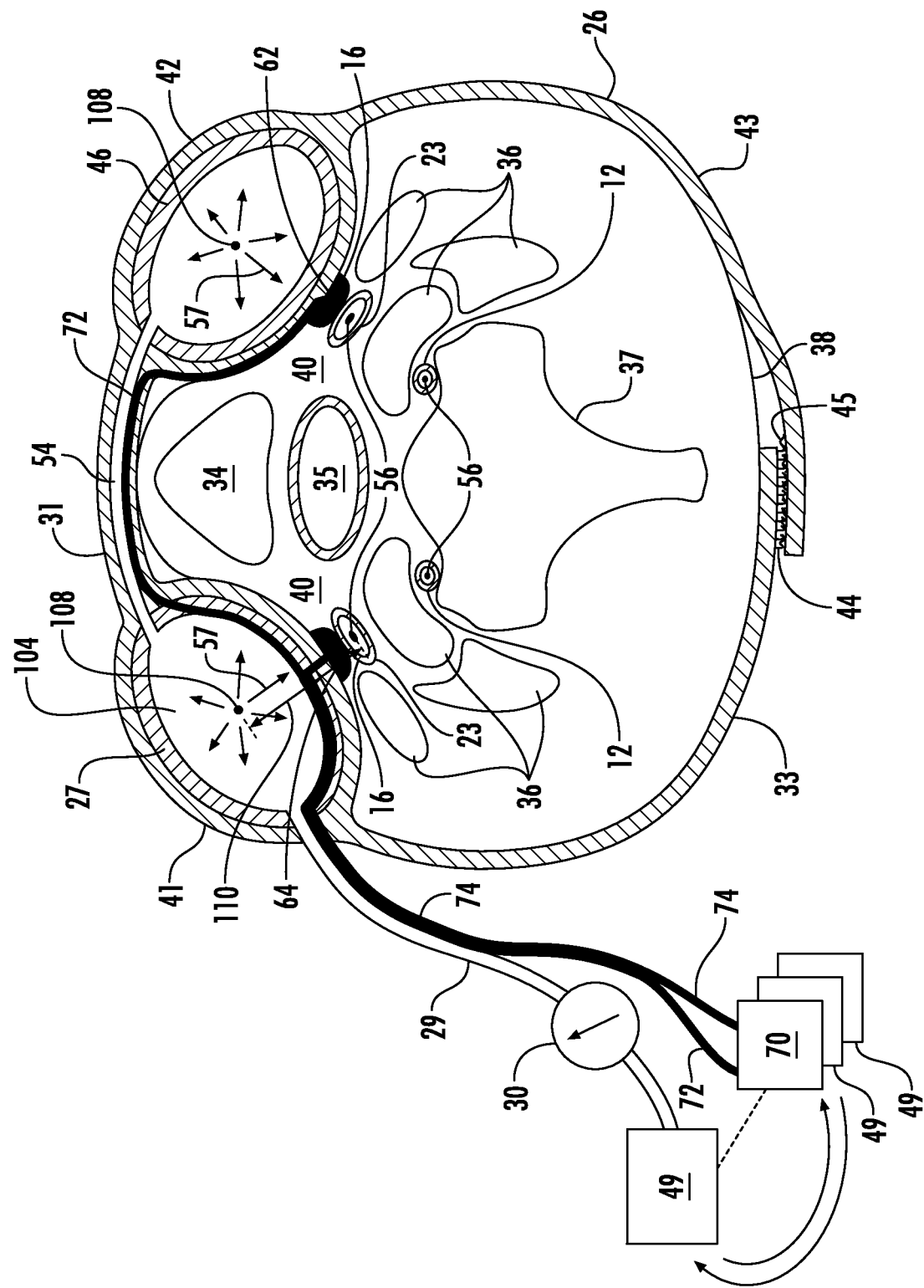
FIG. 8B is a cross-sectional view of a neck of a patient and a device attached thereto in an actuated state.

With reference to FIG. 8A, the vascular probe 64 can be between the neck muscles 36, comprising a sternocleidomastoid muscle, scalenus muscles, omohyoid and longus colli muscles, and the trachea 34 before actuation of the compression member 27. Likewise, the vascular probe 62 may be between the trachea 34 and the neck muscles 36 before actuation. Once actuated, the vascular probes 64, 62 can still be between the trachea 34 and neck muscles 36 (such as sternocleidomastoid muscle, scalene muscles, longus coil muscles and omohyoid muscles), while the actuated compression members 27, 46 are not between the trachea 34 and the neck muscles 36 proximate to their respective right and left carotid arteries 16 as shown in FIG. 8B. Other portions of the patient's neck include the esophagus 35 and the spine that includes the vertebra 37. Also as shown in FIG. 8B, the vascular probe 64 is positioned with respect to the compression member 27 so that the vascular probe 64 is closer to the artery 16 being compressed than the compression member 27. This closeness can be measured by a distance along line 110 that extends from the center of compression 108 to the carotid artery 16. The compression member 27 is farther along this line 110 from the carotid artery 16 than the vascular probe 64 is from the carotid artery 16 along this line 110. The vascular probe 64 can be outside of an interior 104 of the compression member 27 that is the void that is inflated, and the vascular probe 64 may be located on the exterior of the compression member 27. In other versions, the vascular probe 64 is located in the interior 104 such that it is on a wall that defines the interior 104.

Figure 3B:
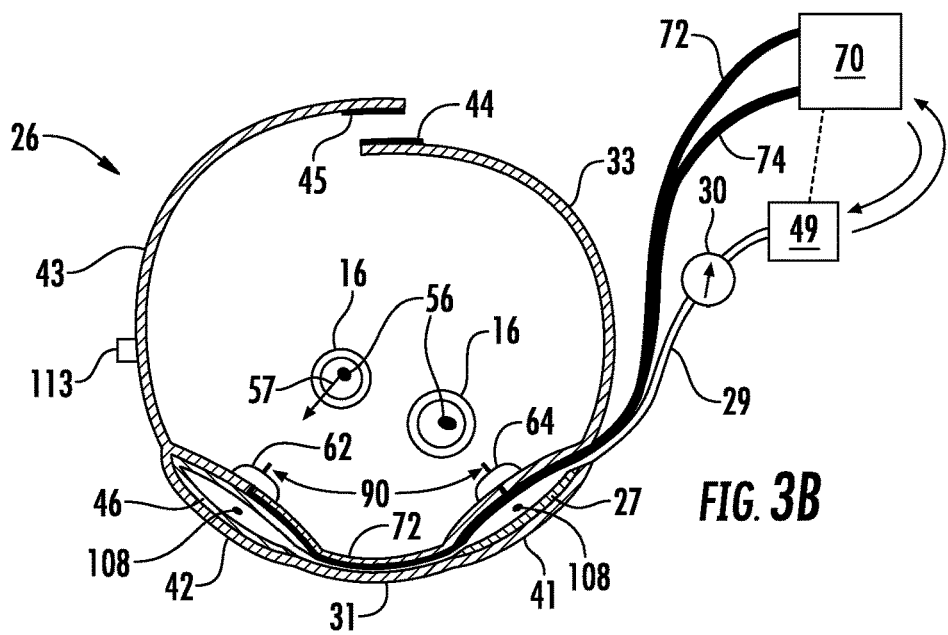
FIG. 3B is a cross-sectional view of the device of FIG. 3A in an unactuated state.
Figure 3C:
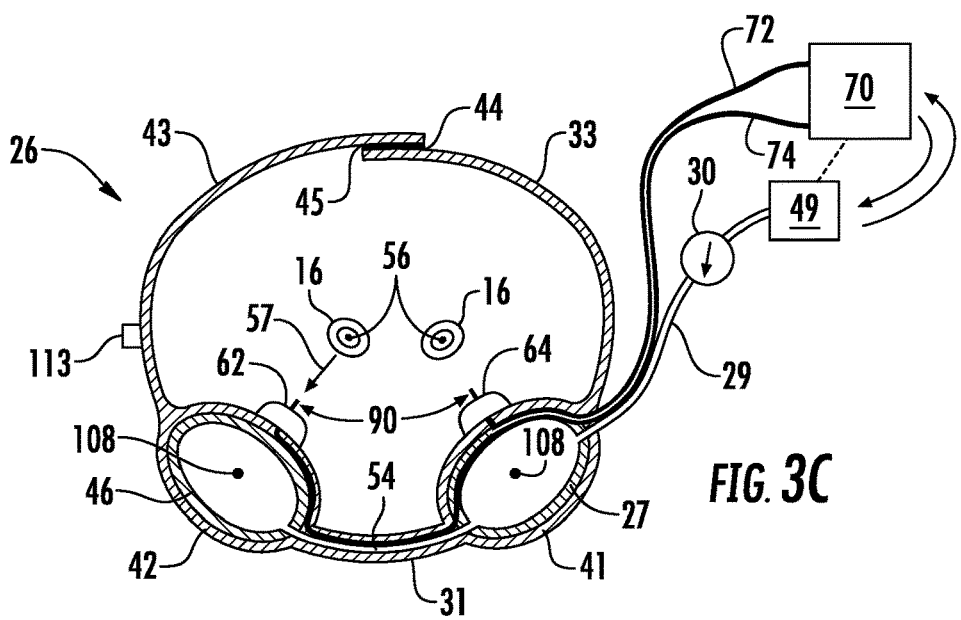
FIG. 3C is a cross-sectional view of the device of FIG. 3A in an actuated state.
Figure 3D:
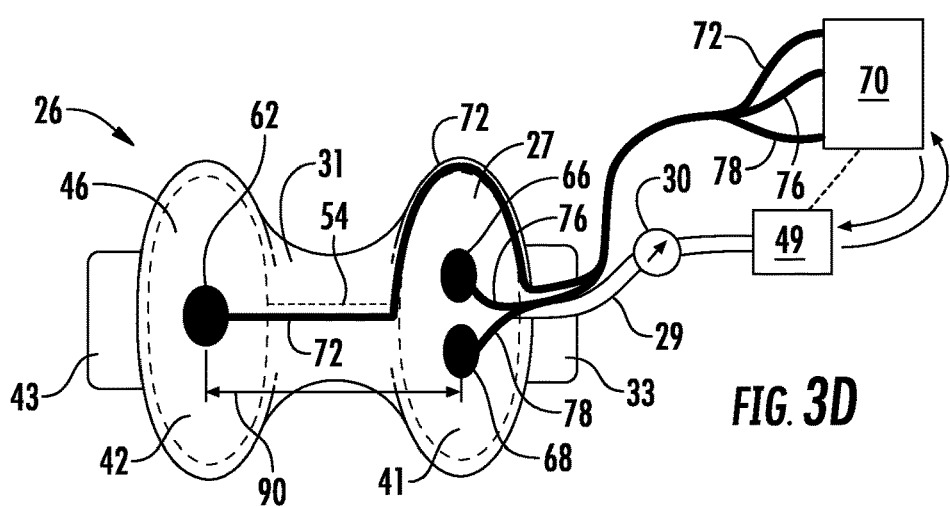
FIG. 3D is a front view of the device of FIG. 3A in an actuated state.

FIGS. 3D and 4 show a schematic representation of the device depicted in FIG. 3B, where the probes 62, 66, 68 may have various positions described above and where the compression members 27, 46 may be represented by members of different shapes as chosen by the health care provider depending on the patient's neck anatomy. For example, such members 27, 46 can be positioned across the neck artery 16, 12 as a compression member 32 and expand either along the longitudinal axis 56, or across the axis 56, or both along and across the axis 56. In other embodiments, as depicted on FIG. 5, the compression members 27 and 46 have an oval shape that is elongated along the longitudinal axis 56 of the artery 16 with the probes 66 and 68 being positioned along the course of propagation of blood and emboli 17, thus providing for measurement of the number of embolic particles, blood velocities, the degree of dampening of the arterial waveform, the degree of pressure gradient and other important parameters both upstream (probe 68) and downstream (probe 66) of the area of compression 23 (probe 62). Probe 62 in this arrangement would provide a B mode imaging of the arterial lumen that can be compared to the similar image obtained from the probes 68 and 66 and would allow one to estimate both visually and mathematically the degree of compression of the artery 16 across its lumen. The degree of compression of the lumen of the artery 16 may vary from 50% to 75%, or up to 100% depending on several factors such as the presence of atherosclerotic plaque, amount of potential cerebral emboli, or desired degree of interruption of cerebral flow. In addition, a combined use of probes 66 and 68 positioned along the course of the carotid 16 or vertebral 12 artery, and optionally probe 62, will be able to provide further information about the course, velocity, intensity and a time lag of propagation of the embolic particles 17 achieving the goal of a much higher sensitivity and specificity of the process of detection of emboli 17, compared to previous devices, such as to TCD.

The straps 33, 43 extend from the pockets 41, 42 to the back of the neck of the patient and on their ends include a fastener such as a hook and loop type fastener. The loops 44 may be on the strap 33, and the hooks 45 can be at the end of strap 43 and they may be affixed to one another to cause the device 26 to be attached to the back of the neck. The device 26 can be arranged so that no force of compression is exerted through pulling of the straps 33, 43, but instead all of the force of compression of the carotid arteries 16 is achieved through inflation or actuation of the compression members 27, 32, 46. The device 26 could have a body 31 that carries the compression member 32 and from which straps 33, 43 extend. However, it may be the case that all of these portions are a single component so that the body 31 in effect is the same as the straps 33, 34 and the straps 33, 34 extend from the body 31. The body 31 has a length in the longitudinal direction 55 that is parallel with the longitudinal axes 56 longer than the lengths of the straps 33, 34 in this direction.

The parameters are processed and analyzed in the input processor 70 and are coupled with the compression mechanisms 49-1 and 49-2 (FIG. 5) leading to actuation or de-actuation of the compression members 27, 46 and/or 32 depending on the basis of the information obtained. For example, if the vascular probe 68 detects the appearance of emboli 17 (embolic signals by ultrasound) it would transmit the signal to the processor 70 that would automatically activate the compression system 49-1 and/or 49-2 and lead to an automatic actuation of the compression members 27, 46 and/or 32, leading to limitation of flow through the arteries 16 and/or 12, thus preventing the emboli 17 from entering the cerebral circulation. An addition, an alarm may be activated to alert the physician about an incoming threat of cerebral embolization and the need to take measures for its prevention. The emboli 17 would then washout into the aorta 9 and distal arteries due to creation of the relative pressure gradient in the arteries 16 and/or 12 and the Bernoulli effect. If the information, obtained from the probe 66, located downstream from the area of arterial compression shows that the emboli 17 are still passing through (persistence of embolic signals detected by probe 66 at a given degree of arterial compression) this information is processed in the processor 70 and leads to further actuation of the compression systems 49-1, leading to further pressurization of the compression members 27 and 46, and a similar compression system 49-2 leading to pressurization of the compression member 32, to achieve a more effective limitation of the flow through the arteries 16 and/or 12. Tubing 47, 48 can connect the compression system 49-1 to the compression members 46, 27 to communicate air or gas for inflation.

A certain acceptable threshold of the number and/or percentage of emboli 17 (embolic signals) passing through may be established to either actuate or de-actuate the compression units 49-1 and 49-2, thus tailoring the degree of arterial compression by members 27, 46 and 32 depending on the relative risk of cerebral embolization weighted against the risk of brain ischemia due to limitation of the blood flow to the brain and the risk of trauma to the arterial intima. For example, further continuation of the compression of the neck arteries 16 and/or 12 by the compression mechanism 49-1, 49-2 may be stopped once the number of embolic signals (that represents the number of emboli 17) registered by probe 66 is decreased by 50% as compared to the number of embolic signals registered by the probe 68, located upstream from the area of the arterial compression. Reaching such a threshold would provide a feedback mechanism from the processor 70 to the compression units 49-1 and 49-2, leading to their de-actuation. In other cases, however, when the amount and the intensity of emboli 17 (number of emboli 17 per second) are very high and, therefore, the risk of embolic stroke is much higher than risks associated with the use of the device 26, such a threshold can be raised to 75% or even 100%. Similarly, depending on the risk of embolization weighted against the risk of limiting the flow to the brain, in some patients, where there is a higher risk of cerebral malperfusion due to limitation of the cerebral flow by virtue of compression of the neck arteries 16 and 12, the degree of arterial 12, 16 compression can be limited to only 50% of the arterial lumen (as detected by the ultrasound probe). However, in other patients where the risk of transient limitation of the cerebral flow is much less than the risk of cerebral embolization, it can be extended to 75% or 100%. Moreover, within the same clinical scenario, the length L1/L2 (FIG. 9) of the compression of the neck artery 16 and/or 12 along its longitudinal axis 56 may vary from 1 to 5 centimeters, for example 1.5 centimeters, 2 centimeters, 2.5 centimeters, 3 centimeters, 3.5 centimeters, 4 centimeters, 4.5 centimeters, or 5 centimeters, thus achieving different degrees of resistance to the influx of emboli 17 to the brain. The longer the segment L1/L2 of the artery 16, 12 compressed, the higher is the degree of resistance to the arterial flow 96, carrying emboli 17.

In addition, further regulation of the blood flow to the brain via the neck arteries 16, 12 can be achieved by varying the time of compression of the arteries 12, 16. The longer the time of compression at each emboligenic event, the lesser is the risk of the brain exposure to embolic injury, yet the higher is the potential for global brain ischemia. The best mode thereof would be to limit the time of compression to 60-90 seconds as in this situation the risk of ischemic brain injury is minimal. However, in patients with hypothermia and on life support, the time of compression of the neck arteries can be extended to 120-180 seconds or longer. All such mechanisms and factors of limiting the inflow 96 of arterial blood (and therefore—arterial emboli 17) to the brain may be used separately or in combination with one another. The resultant effect on the arterial flow 96 is monitored and the cerebral emboli 17 passing through is measured and regulated on the basis of the information obtained from the combination of vascular probes 62, 64, 66, 68, 82, 84 positioned on the compression members 27, 46, 32 of the device. The processing of such data is conducted in the processor 70 and actuation versus de-actuation of the compression mechanism 49, 59 of the neck arteries 16, 12 to obtain optimal parameters of limitation of the cerebral flow in order to protect the brain during brief episodes of embolic washouts. This approach allows a significantly more controllable and safer way of limiting the flow to the brain at the moments of surgery when the risk of embolic stroke is especially high. Optimizing the parameters of arterial compression controlled via 49 and 59 on the basis of the physiological parameters obtained from neck arteries 16, 12 via the feedback system and the processor 70 (FIG. 6) also decreases the risk of and undue trauma to the compressed artery 16, 12, such as trauma to the arterial inner wall, atherosclerotic plaque and the surrounding tissues.

Figure 6:
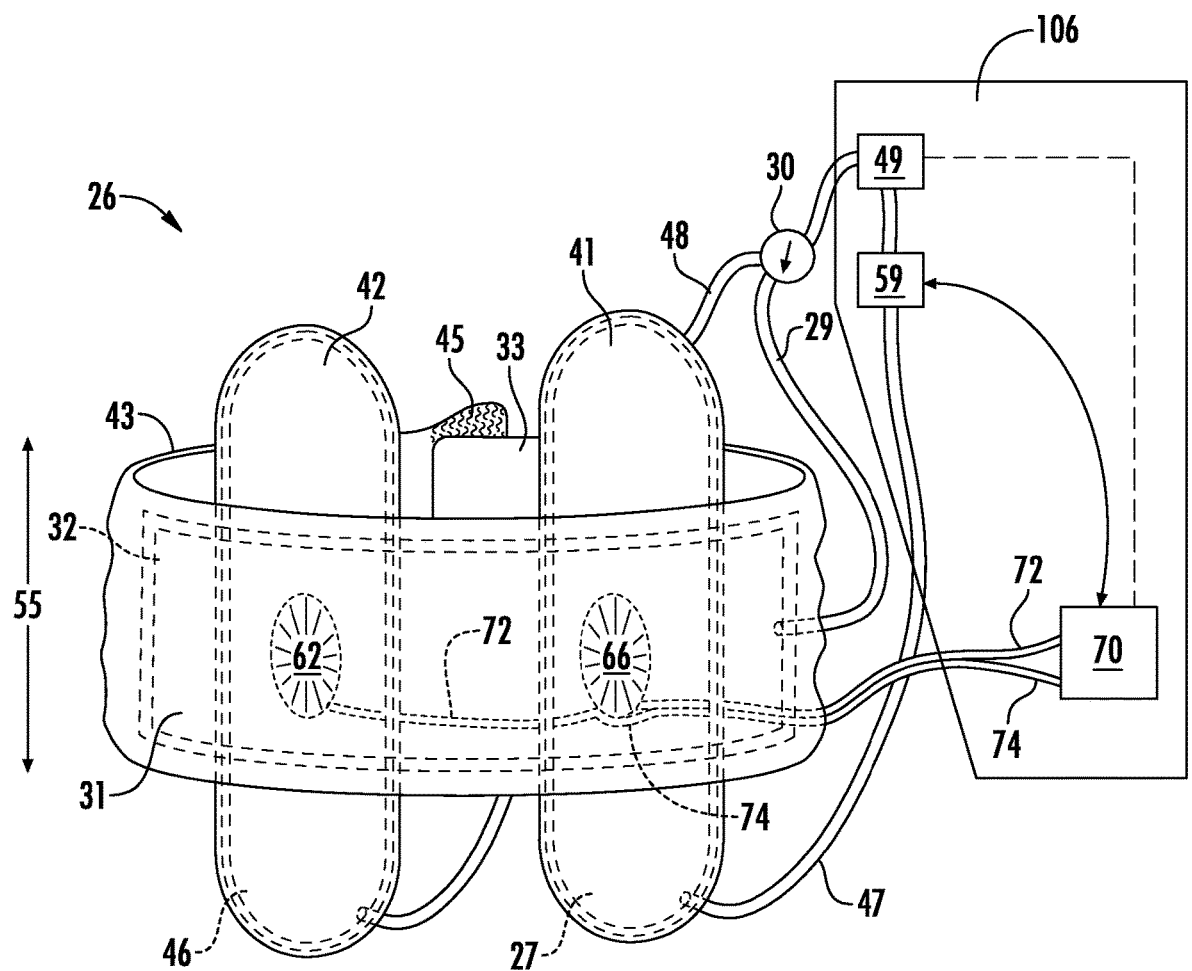
FIG. 6 is a perspective view of a device with monitoring vascular probes attached to the inner surface of the vascular compression members in accordance with another exemplary embodiment.

As depicted in FIG. 6 the information obtained from the vascular probes 62 and 66 may be transferred via cords 72, 74 separately to the processor 70 that interacts with the compression mechanisms 59 and 49, responsible for pressurization of the compression members 27 and 46, positioned along the course of the neck arteries 16 and/or 12, and, in some embodiments, the compression member 32, positioned across the course of the neck arteries 16, 12. Although shown as having two compression mechanisms 49 and 59, only a single one may be included in other embodiments. Further, the various components such as the compression mechanism 49 and processor 70 can be part of the same machine 106, or may be parts of different machines but in communication with one another.

Depending on the data obtained from vascular probes 62, 64, 66, 68, 82, 84, the processor 70 actuates the function of members 27, 46 and, if needed, 32 by regulating the pressure inside the compression members 27, 46, 32 to the level sufficient to achieve a desired level of compression of the neck artery 16, 12, On the basis of the information obtained the compression mechanism 49, 59 is actuated for a defined length of time, to the defined level of pressure in relation to patient's arterial pressure, defined length L of compression and to the desired level of interruption of the carotid and/or vertebral arterial flow 96. A pressure gauge or manometer 30 provides the data regarding the degree of pressurization of the compression member 27, 46, 32, thus reflecting the degree of compression of the underlying neck arteries 16, 12.

Figure 10:
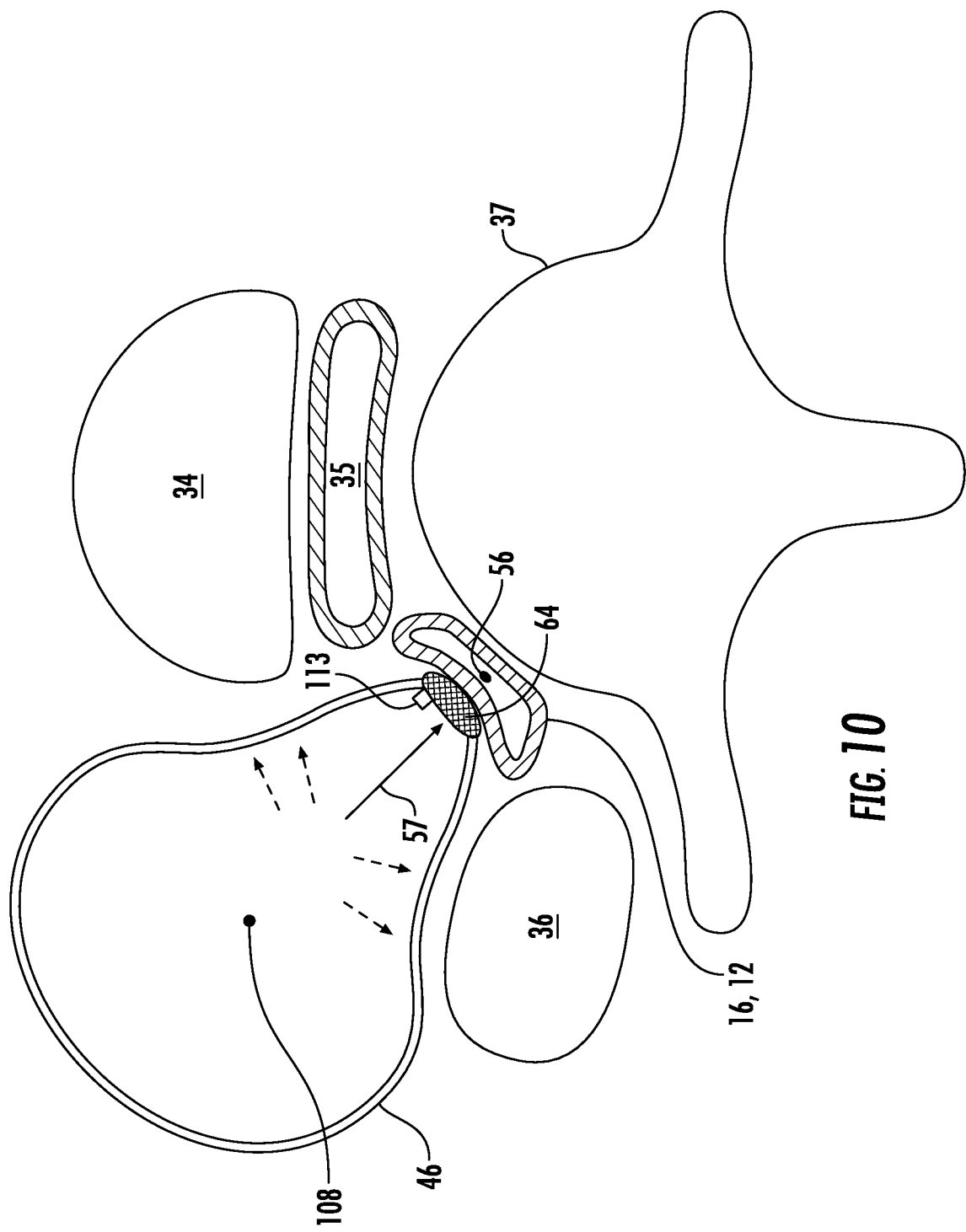
FIG. 10 is a cross-sectional view of a neck of a patient and a device attached in an actuated state with the compression bladder assuming a specific pear shape to assure entering the space between the trachea and the neck muscles while urging the vascular probe against the neck artery in accordance with another exemplary embodiment.
Figure 11:
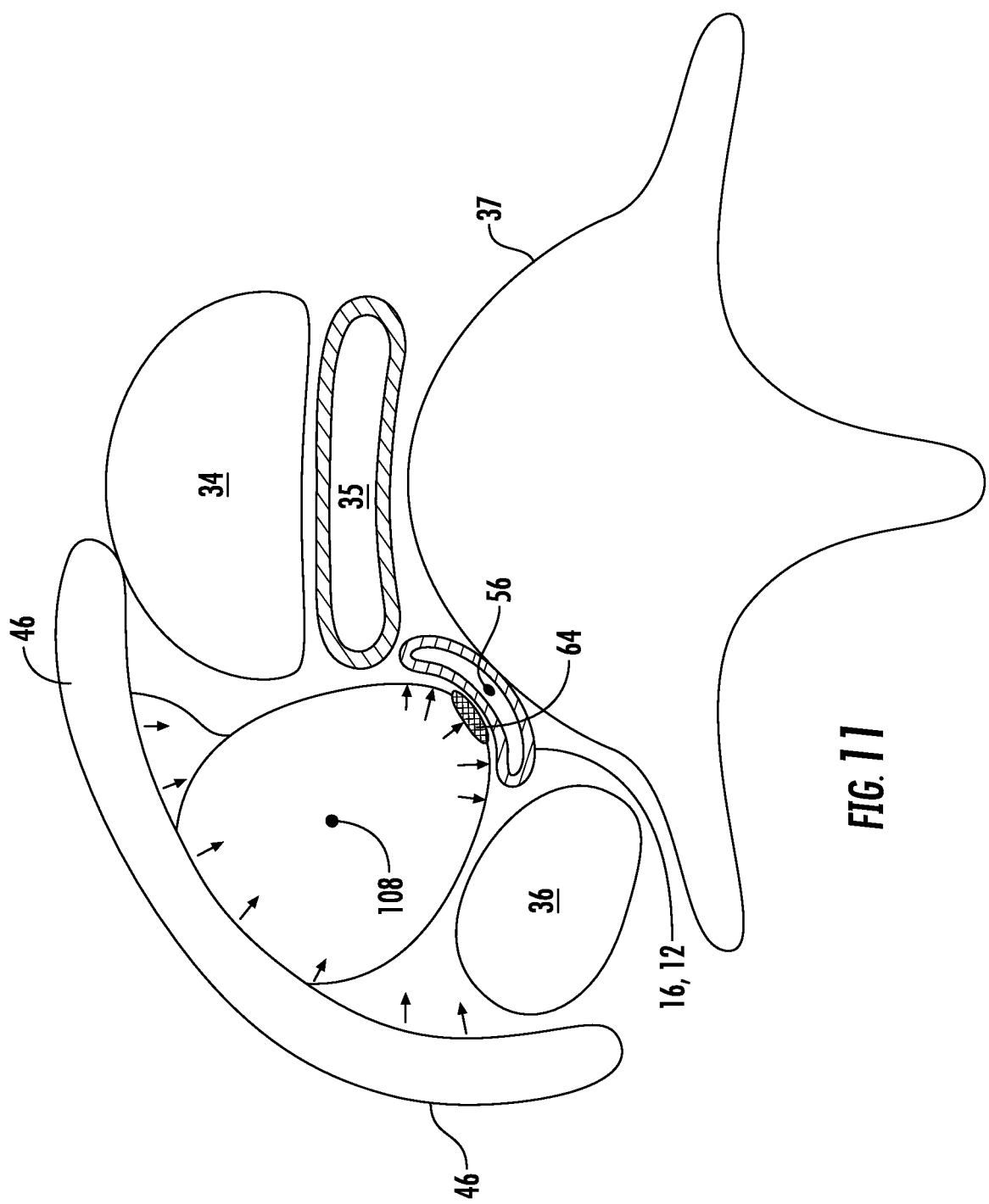
FIG. 11 is a cross-sectional view of a neck of a patient and a device attached in an actuated state with a multicomponent compression bladder assuming a complex specific shape to assure entering the space between the trachea and the lateral neck muscles while urging the vascular probe against the neck artery in accordance with another exemplary embodiment.

Different arrangements of interactions between the processor 70 and the compression apparatuses 49 and 59 can exist with creation of different feedback loops depending on other important physiological parameters that determine the degree of arterial compression, alteration of the vessel lumen, blood velocity, pulse signals, embolic signals, etc. as described previously and the repetition of such mechanisms and arrangements is not necessary. It is also to be understood that the probes 65, 64 and 62, as well as probes 68, 82 and 84 can be positioned together and in different arrangements on both the left (27) and right (46) compression members as well as transverse 32 compression members. FIGS. 8C, 10, 11 and 12 show the vascular probes 62, 64 attached to the most central portions of the compression members 27, 46 and urged against the neck artery 16, 12 leading to an optimal contact with and compression of the artery 16, 12 with an option of a simultaneous vascular imaging monitoring. An enhancement of this technique is using specific shapes of the compression members 27, 46, 32 with thereto attached vascular probes 62, 64, 66, 68, 82, 84 that upon actuation would self-position the central portion of the member 27, 46, 32 and the vascular probe attached 62, 64, 66, 68, 82, 84 to its surface precisely into the anatomic area of the neck artery 16, 12. Such area is located between the trachea 34 medially and the neck muscles 36 laterally. Actuation of the compression member 27, 46, 32 of the disclosed shapes will urge the vascular probe 62, 64, 66, 68, 82, 84 against such artery 16, 12 with the ability of both vascular assessment and compression of the arterial lumen. In this case the specifically designed oval (FIG. 8B), conic (FIG. 8C), pear-shape (FIG. 10), finger-shape (FIG. 12) or combination of shapes with the outer crescent shape type of the compression member 46 as depicted in FIG. 11, would create a specific wedge-like effect, allowing for the member 46 to expand into the anatomic groove between the trachea 34 and neck muscles 36 (such as sternocleidomastoid muscle, scalene muscles, longus colli muscles and omohyoid muscles) urging the probe 64 against the underlying artery 16, 12. As a result, the specific shape that would determine the self-positioning of the compression member 46 upon its expansion directly on top of the neck artery 16, 12 will lead to the most precise and efficient localization and contact between the vascular probe 64 and the artery 16, 12 with the most efficient and anatomically sound compression of the arteries 16, 12 by the vascular probe 64 located on the compression member 46.

Figure 8C:
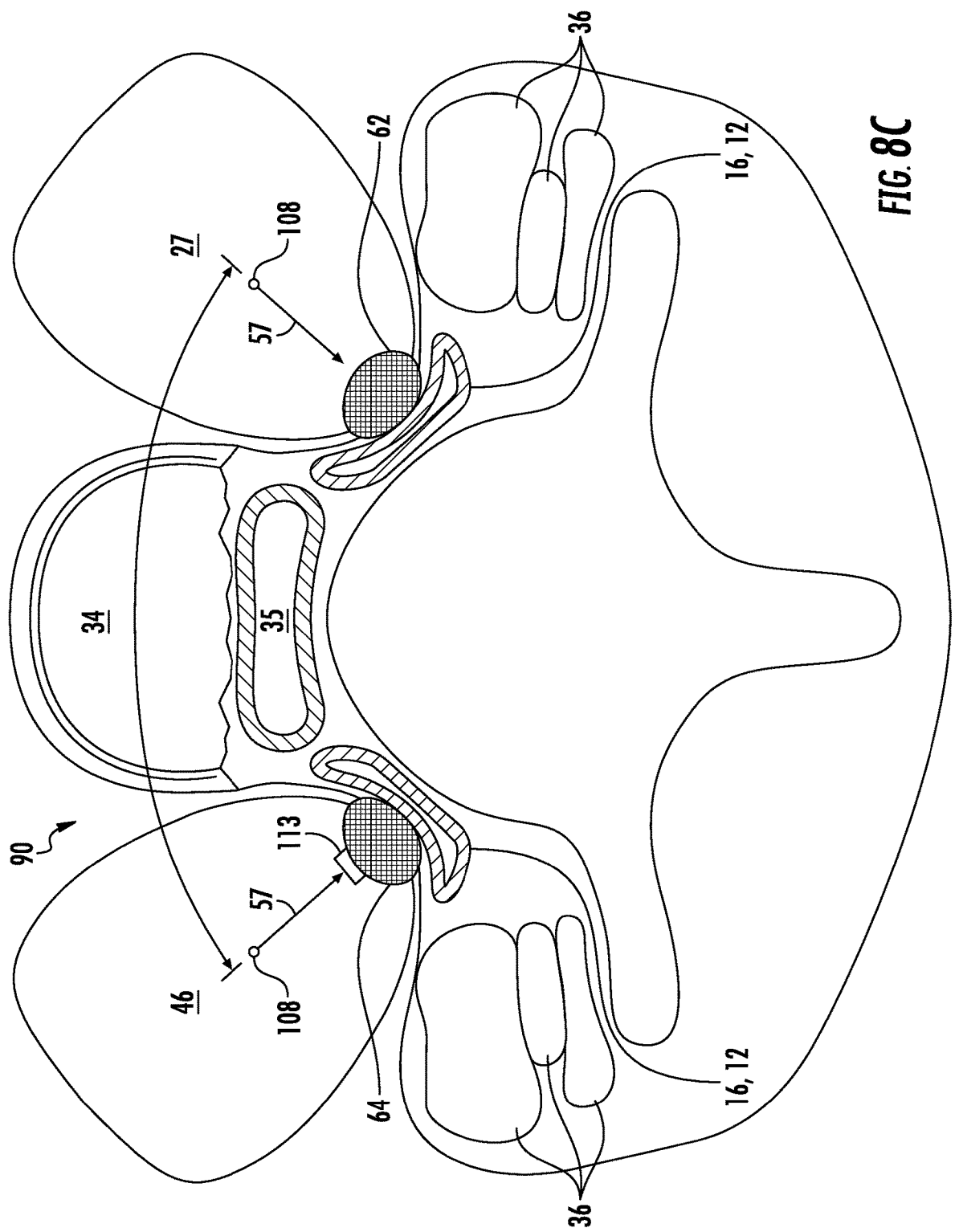
FIG. 8C is a cross-sectional view of a neck of a patient and a device attached in an actuated state with the compression bladder assuming a specific conal shape to assure entering the space between the trachea and the neck muscles while urging the vascular probe against the neck artery.
Figure 12:
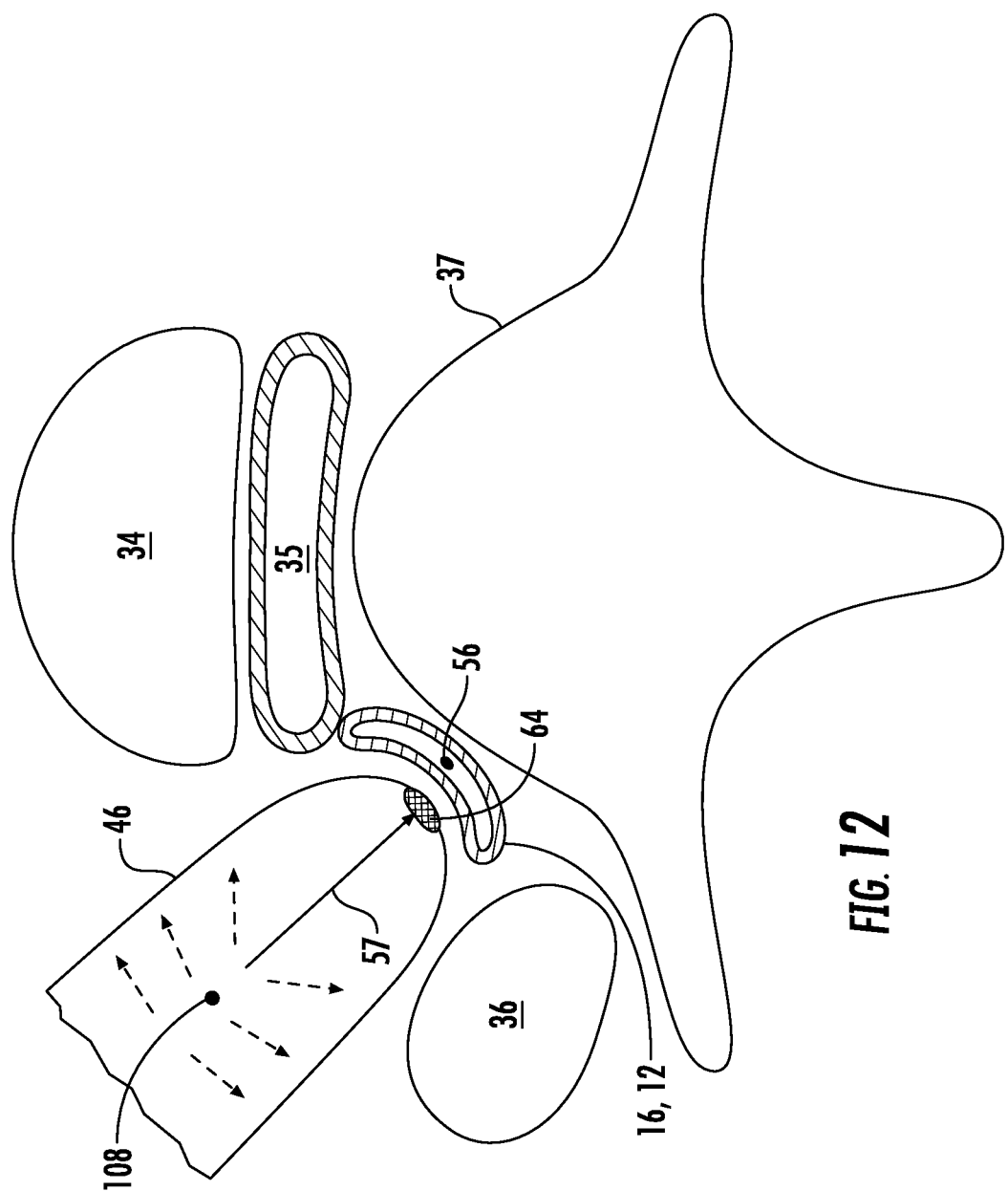
FIG. 12 is a cross-sectional view of a neck of a patient and a device attached in an actuated state with the compression bladder assuming a specific finger-like shape to assure entering the space between the trachea and the lateral neck muscles while urging the vascular probe against the neck artery in accordance with another exemplary embodiment.

The choice of the specific shape of the compression member 46 and vascular probe 64 will depend on the anatomy of the neck and neck arteries 16, 12 in each particular patient and can be determined by the clinical neck assessment, neck measurement, including measuring the depth and positioning of the neck arteries 12, 16, and the assessment of the anatomy of the space between the trachea 34 and neck muscles 36 and the arterial grooves of neck arteries 12, 16 on the basis of the neck CT-scan and ultrasound imaging. For example, in patients with a thin and elongated neck, the most preferred shape of the compression member 46 carrying the vascular probe 64 would be a finger shape, that may be a multiple finger shape (FIG. 12). In a patient with the short neck, it would be an oval shape (FIG. 8B) or conic shape (FIG. 8C). In this case a member 27, 46 with a conic shape (FIG. 8C) would be preferable in patients with significant depth of the neck arteries 16, 12, as can be observed in obese patients. A compression member 46 of a pear shape (FIG. 10) can be used in a patient where the space between the trachea 34 and neck muscles 36 is small (narrow arterial groove). In this case the narrow central portion of the pear-shaped compression member 46 upon its actuation will enter more efficiently into the correct anatomical space urging the vascular probe against the artery 12, 16, while the outer wider portion would stabilize its position over the neck artery 12, 16 by virtue of wedging itself between the trachea 34 medially and the neck muscle 36 laterally (FIG. 10). Considering significant variety of human anatomy, multiple other combinations and arrangements of the shapes, members 27, 32, 46 and vascular probes 62, 64, 66, 68, 82, 84 can be used and the repetition of such arrangements is not necessary. In addition to different shapes and sizes, the compression members 27, 32, 46 and vascular probes 62, 64, 66, 68, 82, 84 may vary in their longitudinal dimension L (FIGS. 9A-9C) at the point of contact between the vascular probe 62, 64, 66, 68, 82, 84 and/or compression member 27, 32, 46 and the neck artery 16, 12 that is being compressed.

The dimension L at the point of contact between the probe 62, 64, 66, 68, 82, 84 and or compression member 27, 32, 46 and the artery 16, 12 may vary from 1 to 5 cm depending on the desired degree of resistance to arterial flow to be achieved. In this situation compression of the neck artery 16, 12 over the 1 cm length (L1 on FIG. 9B) of its longitudinal dimension would produce a lesser amount of resistance to the arterial flow 96 to the brain. As a result while some emboli 17 will be deflected from the brain circulation, other emboli 17 (FIG. 9B) may still pass through the area of compression (FIG. 9B). This arrangement, however, would allow for a better preservation of the cerebral arterial flow 96. Such an arrangement would be most beneficial in patients with a minimal embolic load (such as in coronary artery bypass surgery), where the number of emboli 17 and intensity of the embolic washout, i.e. the number of emboli 17 per second (as detected by the ultrasound probes 62, 64, 66, 68, 82, 84 attached to the compression members 27, 32, 46) are minimal. Conversely, compression of the neck artery 16, 12 over the length of 2, 3, 4 or even 5 cm (L2, FIG. 9C) will produce a much higher resistance to the arterial inflow 96 and the inflow of emboli 17 (FIG. 9C). Such an arrangement will provide a much better deflection of potential emboli 17 (FIG. 9C) from the cerebral circulation with only minimal amount or no emboli 17 at all passing through (FIG. 9C). This arrangement, however, would have a higher risk of compromising the cerebral arterial flow 96 and should be limited to patients with the highest risk of cerebral embolization. For example, such an arrangement would be most beneficial in patients with a maximal embolic load such as in TAVR procedure, where the number of emboli 17 and the intensity of the embolic washout (as detected by the ultrasound probes 62, 64, 66, 68, 82, 84 attached to the compression members 27, 32, 46) are maximal.

The disclosed processor 70 that is monitoring and registering the emboli 17 and is able to trigger an alarm and immediately automatically activate the compression apparatus 49, 59 would allow for the most efficient yet least aggressive degree and time of compression of the neck arteries 16, 12 and therefore would provide the least possible limitation to the cerebral blood flow 96. In addition, the system 26 may allow a health care provider to activate the processor 70 and the compression apparatus 49, 59 ahead of anticipated release of emboli 17 in order to increase the resistance to propagation of emboli 17 into the carotid 16 or vertebral 12 arteries before the release of emboli 17 occurs.

The anatomic arrangement and specific shapes of the compression members 27 and 46 entering the vascular groove between the trachea 34 and neck muscles 36 upon their actuation allows for compression members 27 and 46 to selectively self-position over the neck arteries 16, 12 to create the areas of compression 23 and simultaneous interactive vascular monitoring with the feedback system. The system as described above is designated to activate the alarm and the compression-release mechanism in order to deflect emboli 17 from the carotid arteries 16 and vertebral arteries 12.

With reference in particular to FIG. 3B, a pair of vascular probes 62, 64 is attached to the inner surface of the compression members 27, 46 in such a way that the probes 62, 64 will be urged against the carotid 16 and/or vertebral artery 12 upon actuation of the compression members 27, 46 in such a way that it would both contact and interrogate-monitor the arteries 12, 16. The technique of interrogating and monitoring may comprise ultrasound, flowmetry, pressure measurements, oximetry and other applicable modalities. In addition to standard ultrasound techniques described for ultrasonic assessment of the carotid arteries 16 that have been described before, a new application of carotid ultrasound is disclosed, such as a registration of embolic signals from the level of the carotid 16 and/or vertebral 12 arteries with an option of an automated activation of the carotid 16 and/or vertebral 12 arterial compression system to stop the emboli 17 from entering the brain circulation. To achieve such a goal the specific arrangements in the angle, depth and frequency of insonation have been made that are commensurate with the detection of the high intensity transient signals, obtained by the transcranial Doppler from the level of the cerebral arteries of the head of the patient. The direction of insonation may be either away from the incoming arterial flow while aiming the probe 62 away from the patient's heart 11, or towards the incoming arterial flow 96 while aiming the probe 62 and the direction of insontion towards the patient's heart 11. An automatic adjustment of the probe 62 position on the basis of an optimal ultrasonic flow signal may be provided to facilitate the search for an optimal probe 62 position in each particular patient.

Furthermore, the degree of contact between the probes 62, 64 and the artery may range from a gentle compression of the neck arteries 16, 12 to obtain the diagnostic measurements on one end, and to a significant compression of the arterial lumen in order to produce a pressure gradient leading to deflection of cerebral emboli 17 from the carotid 16 and or vertebral 12 arteries on the opposite end. The degree of compression of the arteries 12, 16 may vary from 5% to 50%, from 50% to 75%, or from 75% to 100% of the volume from the normal at rest volume, with the pressure gradient being between 5 and 60 mm Hg. In some cases the pressure gradient may exceed 60 mm Hg. The shape of the actuated compression member 27, 32, 46 is designed in such a way that it would self position between the trachea 34 and the neck muscles 36 of the patient while the compression members 27, 32, 46 are being actuated. Such a feature is achieved by specifically designed shapes of the compression members 27, 32, 46 aimed at conforming to the patient's neck anatomy and fit into the arterial groove between the trachea 34 and the neck muscles 36 with the predominant expansion towards the central axis 56 of the neck arteries 16, 12 thus urging the vascular probes 62, 64, 66, 68, 82, 84 against the arteries 16, 12 leading to their compression. The probes 62, 64 are configured to face the carotid 16 and/or vertebral 12 arteries and may be attached to the compression members 27, 32 using insertion pockets 41, 42 or may be imbedded into the material of the compression members 27, 32. Vascular probes 62, 64 are connected to the monitoring device 70, where the probe 62 has a separate connection 72 and the probe 64 has a separate connection 74 as depicted in FIGS. 3B and 3C.

In yet another embodiment that is depicted in FIG. 3D one may provide 2 or more probes 66, 68 of similar or different qualities for each compression member 27, 46 while positioning the probes 66, 68 along or across the central axis 56 of the carotid artery 16 or vertebral artery 12. Such an arrangement would allow one to obtain additional information regarding the status of the arterial flow, blood velocity, intensity of embolization and the degree of vascular compression with its effect on the parameters mentioned above. For example, placing vascular probes 66 and 68 in a direction parallel to the central longitudinal axis 56 of each carotid 16 or vertebral 12 artery would allow one to estimate the speed and intensity of propagation of cerebral emboli 17. Using probes 66, 66 with different depth angle and frequencies of ultrasonic waves will allow one to obtain simultaneously the information about the size and composition of the artery (using B-mode of ultrasound), as well as blood velocity (using Doppler mode) and to monitor and calculate the number of embolic signals (using an emboli-detection mode, depth of insonation, angle of insonation and ultrasound frequency). Placing the probe 66, 68 across the long axis 56 of the artery 16 would allow one to assess the cross-section of the artery 16 and to assess the degree of its compression. Obtaining all this information during the medical procedure that is known to produce cerebral emboli will provide valuable information that is necessary to immediately initiate measures for prevention of embolic stroke such as automated or operator triggered temporary compression of the carotid arteries 16. In this setting the compression may be initiated in an automated fashion after coupling the information obtained from the vascular probes 62, 64, 68 sent to monitoring device 70 and coupled with the compression apparatus 49 that would trigger actuation of compression members 27 and 46 using a positive vs. negative feedback mechanism of actuation (FIGS. 3B-3D). In this case the appearance of emboli 17 as detected by the probe set for detection of embolic signals would trigger an actuation of the compression member 27, 46, while the disappearance of embolic signals may initiate the release of the arterial compression and the reestablishment of the carotid and vertebral blood flow. Probe 66 can be in communication with processor 70 via electric cord 76, and probe 68 can be in communication with processor 70 via electric cord 78 so that information from both probes 66, 68 is communicated to the processor 70. The probe 62 can likewise be in communication with processor 70 through electric cord 72. In some arrangements, however, a wireless communication between the probes 62, 68 and the processors 70 can be established by incorporating an intermediate microprocessor 113 into the neck collar. Such microprocessor 113 can be located within the area of the compression member 27, neck strap, or be removably attached to the outer surface of the neck compression collar. The wireless arrangement will provide further improvement and feasibility of using the device 26 to reach the goal of a combined detection and prevention of cerebral emboli 17.

The compression members 27 and 46 can be elongated so that they are longer when actuated in the longitudinal direction 55 than in the lateral direction. The compression members 27, 46 can expand so that they are longer than the length of the straps 33, 43 in the longitudinal direction 55. The longitudinal direction 55 is parallel to the longitudinal axis 56. The vascular probes 66 and 68 are spaced from one another in the longitudinal direction 55, yet are configured to face the carotid 16 and/or vertebral 12 arteries.

Members 27 and 46 are shown in a deflated or unactuated state in FIG. 3B and may be made of a flexible material that can be stretched or otherwise deformed. The material making up members 27, 46 can be nonporous such that members 27, 46 are capable of being filled with gas or liquid that enables members 27, 46 to expand and at the same time hold the gas or liquid therein. The design of the members 27, 46 may differ depending on the specifics of the patient's anatomy such as the distance between the trachea 34 and the sternocleidomastoid and/or scalene muscles, omohyoid and longus colli 36, the depth of the carotid 16 and or vertebral arteries 12 and the dimensions of the anterior triangle of the neck. The members 27, 46 and/or 32 may be either oval (FIGS. 8A and 8B), conal (FIG. 8C), pear-shaped (FIG. 10), crescent shaped (FIG. 11), finger shaped (FIG. 12), or any combination of said designs (FIG. 11) to achieve the most effective and safest compression of the carotid 16 and or vertebral artery 12 with the least possible trauma to the arterial wall.

As depicted in FIGS. 9A, 9B and 9C, the design of the described compression members 27, 32, 46 may comprise a feature of a longitudinal extension L, i.e. extension of the compression member 27, 32, 46 along the central longitudinal axis 56 of the artery 16, 12 with an option of compression of the artery 16 along its course using the advantage of creating a higher resistance to the arterial flow by virtue of increasing the length L of the compression area along the artery from L1 to L2 (FIG. 9C).

According to the Poiseuille equation, the resistance to flow is proportional to the length of the narrowed portion of the vessel. Therefore, increasing the length of the compressed area along the longitudinal axis 56 of the artery from L1 to L2 along the axis 56 (FIGS. 9B and 9C) will be associated with an incremental rise of the resistance to the arterial inflow 96 (and consequently the inflow of potential cerebral emboli 17) at any given degree of arterial compression across the arterial lumen.

For example, in spite of the same degree of compression of the arterial lumen (diameter) in the artery 16, depicted on FIG. 9B, the inflow of emboli 17 to the artery 16 and the passage of emboli 17 through its lumen will be less affected as in the artery 16 where the length of the compression area along the central axis 56 of the artery 16 is longer (L2 in FIG. 9C vs. L1 in FIG. 9B). From this perspective it would be more effective and safe to achieve compression along the central axis 56 of the artery 16, while limiting the degree of compression across its lumen, the latter being more damaging to the arterial wall.

Figure 13:
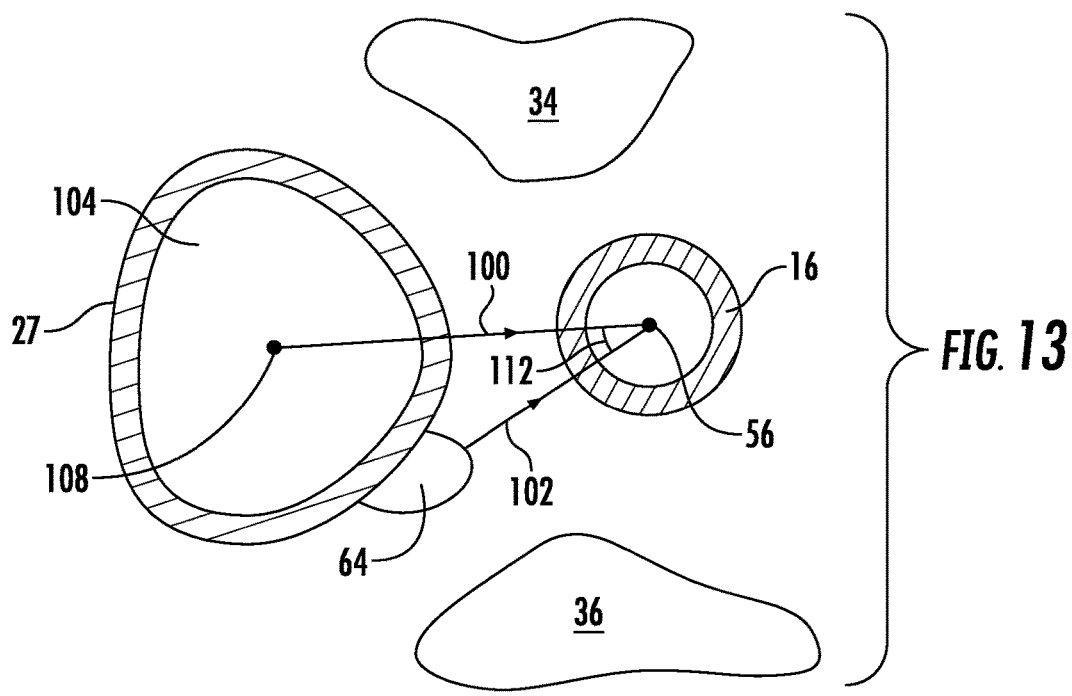
FIG. 13 is a partial cross-sectional view of a neck of a patient with a compression member actuated in which the vascular probe is closer to the carotid artery than the compression member.

FIG. 13 is a top view in cross-section of the device 26 attached to the neck of the patient and inflated so that pressure is being applied to the carotid artery 16. The pressure applied by the compression member 27 is aligned and extends in a direction of force 100 from the center 108. The direction of the compression force 100 lies along a line that extends from the center 108 to the central axis 56 of the carotid artery 16. The vascular probe 64 is on the exterior of the compression member 27 and is not in alignment with this direction of force 100. In this regard, the vascular probe 64 receives a signal or sends a signal to the carotid artery 16 and this sending (or receiving) is shown as signal 102 and extends along the line indicated by this reference number. Signal 102 extends along a line from the vascular probe 64 to the central axis 56. The signal 102 is at an angle 112 to the direction of force 100, and this angle may be from 15 degrees to 40 degrees in certain exemplary embodiments, and cart be from 0 degrees to 60 degrees, or from 15 degrees-60 degrees in other embodiments. By placing the vascular probe 64 at an angle 112 from the direction of force 100 exerted by the compression member 27 in accordance with the physics of the Doppler ultrasound, it may be much easier and more accurate to measure certain parameters of the carotid artery physiology and hemodynamics 16 such as detection of emboli 17.

Figure 15:
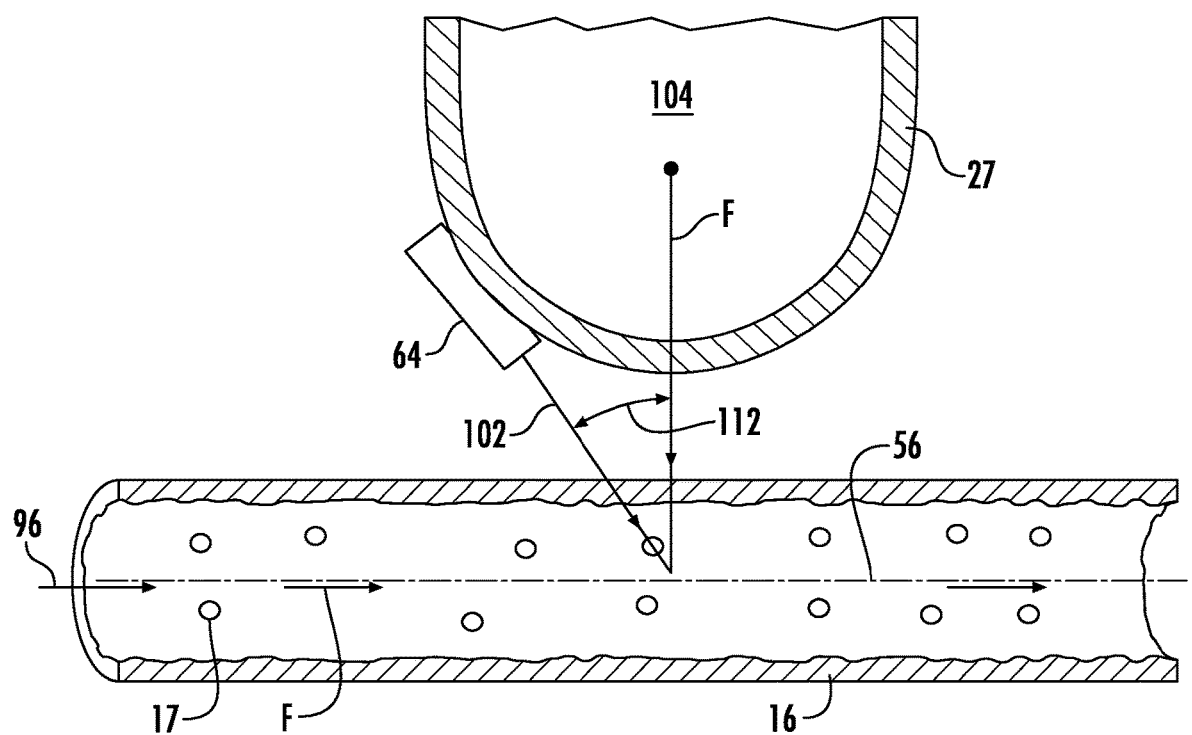
FIG. 15 is a partial cross-sectional view of the compression member that carries a vascular probe that is at an angle to a direction of force of the compression member oriented with a component in the direction of travel of the blood flow.

FIG. 15 shows another embodiment of the device 26 in which the vascular probe 64 emits the signal 102 that is at an angle 112 to the direction of Force F exerted by the compression member 27 when it actuates to apply the compressive force. The view is rotated 90 degrees from that shown in FIG. 13 and the direction of signal 102 includes a component that is in the direction of flow F of the blood flow through the carotid artery 16. The signal 102 could alternatively be arranged at an angle 112 that is on the other side of the compression member 27 and hence have a direction with a component that is upstream of the direction of flow F. The angle 112 could be variously arranged as described above (for example from 15 degrees to 60 degrees in some embodiments).

Figure 14:
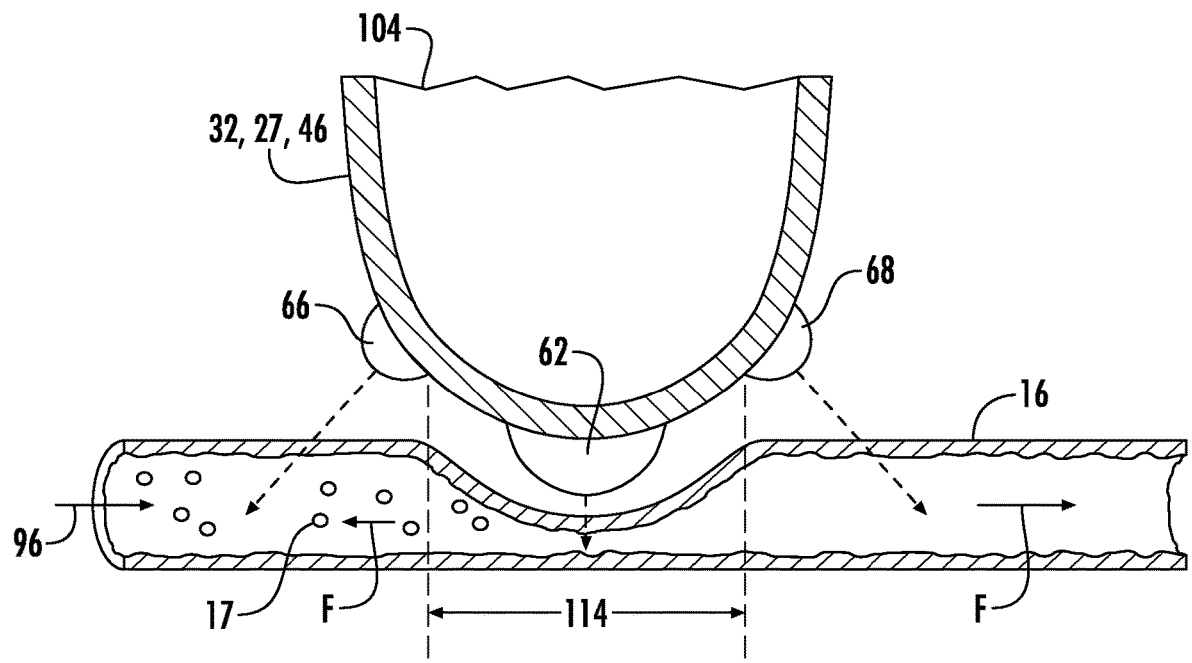
FIG. 14 is a partial cross-sectional view of a compression member that carries three vascular probes in which each probe is located at a different position relative to an area of compression.

FIG. 14 shows an embodiment of the device 26 in which the compression member 32, 27, 46 expands to cause an area of compression 114 to be imparted onto the carotid artery 16. The compression member 32, 27, 46 carries three vascular probes 66, 62, 68 outside of its interior 104. Vascular probe 62 is located at the area of compression 114 and measures a parameter of the carotid artery 16 that is at the area of compression 114. Vascular probe 66 is located outside of and upstream from the area of compression 114 so that it measures a parameter of the carotid artery 16 that is upstream from the area f compression 114 in the flow direction F to ascertain a different parameter or the same parameter just at a different location of the carotid artery 16. This location can provide different information that can be compared to the data obtained by vascular probe 62. Vascular probe 68 is located downstream from the area of compression 114 and is outside of the area of compression 114. Vascular probe 68 can thus obtain data that is different from the data from probes 62 and 66 and can provide other insight into the process. This arrangement of vascular probes 62, 66, 68 can yield varied information on the effectiveness of the compression and the transport of emboli 17 through the carotid artery 16.

FIGS. 16-A and 16-6 show an embodiment of the device 26, where the position and the angle of the vascular probe 68 as well as the angles of insonation Alpha and Beta may be changed depending on the degree of actuation of the compression member 32, 27, 46. As shown in FIG. 16-A a compression member 27, carrying the probe 68 will initially position the probe 68 at the angle Alpha ($\alpha$) in relation to the underlying artery 16. However, upon actuation of the member 27 by virtue of inflation, the vascular probe 68 may change its position and the angle of insonation in relation to the artery from $\alpha$ to Beta ($\beta$), where the angle $\alpha$ is smaller than the angle Beta ($\beta$). Similarly, as shown in FIG. 16-B a plurality of vascular probes 62,66,68 in a variety of arrangements may be located on the compression member 32, 27, 46 in such a way that further expansion of the compression member 32, 27, 46 may bring some of these probes 62, 66, 68 into a different position both in relation to the area of the artery 16 and the degree of its compression and the angles of insonation Alpha and Beta in relation to the underlying artery 16. As a result, the angle of insonation Alpha-1 of the midline probe 62 may not change and may be equal to Beta-1 after the compression member 27 is actuated, however the angles Alpha-2 and Alpha-3 of adjacent probes 66, 68 will increase respectively to Beta-2 and Beta-3. Such changes in the probe 66, 68 position and the angle of insonation in relation to the underlying artery 16 achieves a goal of adjusting and improving the probes 66, 68 and the device's ability to obtain the necessary parameters such as blood flow, velocity, imaging and detection of embolic signals throughout the course of the procedure.

One feature of the device 26 is the ability to both register embolic signals from the level of the carotid 16 and/or vertebral 12 arteries and to interrupt the flow of emboli 17 to the brain before they reach the brain. The device 26 does not detect cerebral emboli at the level of cerebral arteries when the emboli 17 have already reached the brain i.e. at the latest stage of their progression, as it is done by transcranial Doppler ultrasound. At this point, stroke would occur and nothing could be done.

In this aspect, combining a feature of detecting the emboli 17 upstream from the brain (i.e. at the earliest stage of their progression, when they are just at the level of the carotid 16 and vertebral 12 arteries), plus the ability to prevent them from entering the brain by virtue of carotid 16 and/or vertebral 12 artery compression achieved within the same device disclosed herein, will provide for both diagnosis and immediate treatment of this condition. The device 26 provides for a real time mechanism to deflect such emboli 17 as soon as they are detected, using either man operated or automated technology. One way of accomplishing this is with a specific ultrasound probe 62 working at the specific depth, frequencies and angles of insonation commensurate with the function of detection of cerebral emboli 17, that is suitable to detect the echo signals from the moving embolic particles (solidi vs. gas) from the level of the carotid 16 and vertebral 12 arteries at the neck of the patient (and not at the level of the head and skull as a transcranial Doppler device). For Example, while the depth of insonation for detection of embolic signals using a standard transcranial Doppler device is 5-6 cm, the disclosed parameter of depth for detection of emboli passing through the carotid artery 16 is 1-5 cm, while the angle is 0-60 degrees. Moreover, if the insonation frequency required for detection of emboli 17 by transcranial Doppler can not exceed 2 MHz, the range of insonation frequencies to detect cerebral emboli 17 using our device is much wider, ranging from 1.5 to 8 MHz as there is no cranial (skull) interface between the vascular probe 62 and the artery 16, 12 that is examined. Moreover, inflating the expandable member 27 that is configured to face the underlying carotid 16 and/or vertebral 12 artery upon its actuation will achieve an adequate positioning of the ultrasound probe 62, 64, 66 against the artery 16, 12 with the improved sensitivity and specificity of the ultrasound readings and a better ability to differentiate embolic signal from the baseline blood flow. Once the compression members 27, 32, 46 are actuated and the distance between the ultrasound probe 62, 64, 66 and the artery 16, 12 is diminished, the depth of insonation required for detection of cerebral emboli may be also decreased to 4 cm, 3 cm, 2 cm or even 1 cm.

In addition, in some embodiments an actuation, or deactuation of the compression members 27, 32, 46, carrying the vascular probe 64, 66, 68 on its surface may allow for adjustment of the angle of insonation between the axis of insonation of the probe 64, 66, 68 and longitudinal axis 56 of the blood flow between the artery 16, 12. Such an adjustment may be achieved by virtue of changing the plane and the geometry of the compression member 27, 32, 46 in relation to the underlying artery 16, 12 upon actuation. As a result a number of optimal probe 64, 66, 68 positions and insonation algorithms for the detection of embolic signals from the level of the neck arteries can be achieved depending on the probe frequency, its depth, angle of insonation etc. For example, with the 1.6-8.0 MHz probes 64, 66, 68 the optimal parameters for detection of both carotid flow and embolic signals would be the Depth of 22±4 mm, gain 18±3, Amps 33±5 and the angle of 30±5.

The actuation of the compression member 27 can change the angle that the vascular probe 64 is oriented to the central axis 56 some amount. The amount of change may be from 0 percent to 90 percent in certain exemplary embodiments. This angle may be angle 112 or may be the alpha, beta angles as previously discussed.

In addition, the information obtained from the level of the carotid 16 and/or vertebral 12 arteries may be coupled with the other ultrasonic characteristics obtained in the process and may be used to start an automated response that would initiate compression of the carotid 16 and/or vertebral 12 arteries when necessary.

The device 26 can be arranged so that the compression member 27 and the vascular probe 64 are at the neck of the patient or lower and no portion of the device 26 wraps around the head of the patient. In this regard, the device 26 can be arranged so that nothing is worn on the head of the patient, such as would be the case when ultrasound Doppler headsets, frames, helmets or the like are worn on the head of the patient. The entire compression member 27 and vascular prove 64 may not be located at the head of the patient, but instead from the chin or neck lower towards the feet. With this arrangement, the device 26 can detect emboli 17 at neck level and need not send a signal 102 through the skull. The wave frequency may be higher than those that sense through the skull. The frequency of signal 102 may be 1.5 MHz up to 8 MHz, in other embodiment greater than 2 MHz, and in other embodiments from 2.1 MHz-8 MHz, and the depth of insonation may be 1-5 centimeters (instead of 5-6 centimeters as would be the case otherwise). The device 26 can be arranged so that none of the signals 102 from any of the vascular probes 64 travel through the skull.

The device 26 provides for both detection of emboli 17 and prevention of emboli 17. The device 26 is thus diagnostic and preventive, and when signals 102 extend though the neck and not the skull, it can prevent a 90 percent loss of the signal that would otherwise be the case. The detection features may occur at the neck of the patient and not in the brain, and thus detect and prevent the emboli at a much earlier stage of their propagation. Further, in some embodiments in which the device 26 is below the head of the patient and thus from the neck down the absence of probes 64 on the head affords a clearer picture since the picture may shift constantly and get lost as the patient turns his or her head.

It is to be understood that as used herein, the term "closed" when referring to the neck arteries, such as the carotid artery 16 and vertebral artery 12, means that a cut is not made into the skin or the artery 16, 12. The neck arteries 16, 12 could be externally accessed (such as by a catheter or other device) entering a downstream artery and then moving into the arteries 16, 12, and still be closed because the neck arteries are not cut open. As such, "closed" neck arteries 16, 12 also includes those that are and are not externally accessed. When referencing a closed artery 16, 12 the present application is not referring to one that is blocked by emboli 17 or other obstructions, although it could be in some embodiments, but is rather referring to one that is not cut open by an incision through the neck. The neck arteries 16, 12 may be externally accessed through a downstream artery but not externally accessed through the neck itself when the device 26 performs diagnosis and prevention.

While the present invention has been presented in connection with certain preferred embodiments, it is to be understood that the subject matter encompassed by way of the present invention is not to be limited to those specific embodiments. On the contrary it is intended for the subject matter of the invention to include all alternatives, modifications, and equivalents as can be included within the spirit and scope of the following claims.

What is claimed:

1. A device for the prevention of stroke, comprising:
   a processor;
   a compression system;
   a compression member that is inflatable wherein a wall of the compression member defines a void of the compression member; and
   a vascular probe that is carried by the compression member and is imbedded into material of the compression member that makes up the wall such that air or gas that goes into the void and inflates the compression member comes into contact with the vascular probe, and wherein the vascular probe extends completely through the wall such that a portion of the vascular probe is uncovered by the compression member, wherein the vascular probe is adapted to sense a parameter of a circulation system of a patient, wherein the parameter that is sensed is from a closed neck artery that is not being externally accessed through skin of a neck when the parameter is sensed such that the parameter is a closed parameter, and wherein the sensed closed parameter is communicated to the processor, wherein the processor processes the closed parameter and based upon this processing communicates with the compression system to instruct the compression system to actuate the compression member to apply compression to the closed neck artery;
   wherein the compression member and vascular probe are adapted to be external to the interior of the patient when the vascular probe senses the closed parameter of the circulation system;
   wherein the vascular probe is adapted to change position closer and farther relative to the closed neck artery and is adapted to change an orientation angle relative to the closed neck artery upon an increase in expansion of the compression member such that the parameter of the circulation system that is adapted to be sensed is sensed both before and after the change in position and the change in orientation angle;
   wherein after the actuation of the compression member the vascular probe is configured to sense the presence of emboli in the closed neck artery and communicates the presence of emboli to the processor, wherein the processor processes the presence of emboli after the actuation of the compression member and based upon this processing communicates with the compression system to instruct the compression system to further actuate the compression member to increase the amount of compression onto the closed neck artery.

2. The device as set forth in claim 1, wherein the processor and the compression system are part of the same machine.

3. The device as set forth in claim 1, wherein the vascular probe comprising an ultrasound probe, a flow probe, an oximeter probe, or a pulse probe.

4. The device as set forth in claim 1, wherein the sensed closed parameter that is sensed by the vascular probe comprising blood velocity, blood flow, diameter of an artery, or an anatomical extent of compression.

5. The device as set forth in claim 1, wherein the sensed closed parameter that is communicated comprising embolic signals, pulse signals, or oximetry signals.

6. The device as set forth in claim 1, wherein the sensed closed parameter that is sensed by the vascular probe comprising a degree of reduction of an arterial lumen, a degree of compression of the artery along a length of the artery, a scanned image of an artery, detection of embolic particles, regional and systemic arterial pressures, number of embolic particles that are deflected versus the number of embolic particles that pass through the artery, an intensity of an embolic load that is represented by a number of embolic signals per second, or the calculated degree of the transverse and longitudinal carotid compression required to deflect each particular embolic load.

7. The device as set forth in claim 1, wherein the vascular probe is adapted to sense multiple parameters of the circulation system of the patient from the closed neck artery, and wherein the sensed multiple closed parameters are communicated to the processor, wherein the processor processes the sensed multiple closed parameters and based upon this processing communicates with the compression system to instruct the compression system to actuate the compression member.

8. The device as set forth in claim 1, wherein the closed neck artery is a carotid artery, wherein the vascular probe is a first vascular probe, and further comprising a second vascular probe that is carried by the compression member, wherein the second vascular probe is adapted to sense a parameter of the circulation system of the patient that is from the closed carotid artery, and wherein the sensed closed parameter from the second vascular probe is communicated to the processor, wherein the processor processes the sensed closed parameter from the second vascular probe and based upon this processing communicates with the compression system to instruct the compression system to actuate the compression member;
wherein the compression member compresses the closed carotid artery when actuated, wherein the first vascular probe and second vascular probe are adapted to be located adjacent the closed carotid artery and the first vascular probe is adapted to be located upstream from the second vascular probe in the direction of blood flow through the closed carotid artery.

9. The device as set forth in claim 1, wherein the compression member is actuated in order to compress the closed neck artery, and wherein the processor instructs the compression system to actuate the compression member such that an area of compression of the closed neck artery is adjustable along a flow direction length of the closed neck artery from 1 to 5 centimeters.

10. The device as set forth in claim 1, wherein the vascular probe is a first vascular probe and wherein the closed sensed parameter that is sensed by the first vascular probe is a velocity of blood flow through the closed neck artery; and further comprising:
a second vascular probe that is adapted to sense a parameter of the circulation system of the patient that is from the closed neck artery that is an image of the closed neck artery, and wherein a sensed image of blood flow from the second vascular probe is communicated to the processor;
a third vascular probe that is adapted to sense a parameter of the circulation system of the patient that is from the closed neck artery that is an amount of emboli that is flowing through the closed neck artery, and wherein the sensed amount of emboli that is flowing through the closed neck artery from the third vascular probe is communicated to the processor.

11. The device as set forth in claim 1, wherein the vascular probe that is carried by the compression member is a first vascular probe, and further comprising:
a second vascular probe that is carried by the compression member, wherein the second vascular probe is adapted to sense a parameter of the circulation system of the patient, wherein the parameter that is sensed by the second vascular probe is from the closed neck artery that is not being externally accessed when the parameter is sensed such that the parameter sensed by the second vascular probe is a closed parameter, and wherein the sensed closed parameter from the second vascular probe is communicated to the processor; and
a third vascular probe that is carried by the compression member, wherein the third vascular probe is adapted to sense a parameter of the circulation system of the patient, wherein the parameter that is sensed by the third vascular probe is from the closed neck artery that is not being externally accessed when the parameter is sensed such that the parameter sensed by the third vascular probe is a closed parameter, and wherein the, sensed closed parameter from the third vascular probe is communicated to the processor;
wherein actuation of the compression member causes an area of compression to be imparted onto the closed neck artery, wherein the first vascular probe is adapted to be located upstream from the area of compression in the flow direction of the closed neck artery, wherein the second vascular probe is adapted to be located downstream from the area of compression in the flow direction of the closed neck artery, and wherein the third, vascular probe is adapted to be located at the area of compression of the closed neck artery.

12. The device as set forth in claim 1, wherein the compression member when actuated creates a force that extends in a direction of force to the closed neck artery, wherein the vascular probe emits a signal into the closed neck artery, wherein the vascular probe is located on the compression member such that the direction of the signal is not parallel to the direction of force and is oriented at an angle that is from 0 degrees-60 degrees to the direction of force.

13. The device as set forth in claim 1, wherein the compression system is adapted to be activated on demand by a health care provider in anticipation of an embolic event to achieve preemptive protection of cerebral circulation from upcoming emboli that is triggered manually by the health care provider.

14. The device as set forth in claim 1, wherein the neck artery is a vertebral artery.

15. The device as set forth in claim 1, wherein the parameter that is sensed is embolic particles that are detected within the neck artery at an angle of insonation of the vascular probe and the neck artery between 0 and 60 degrees with a depth of insonation between 1 and 5 centimeters and with an insonation frequency ranging between 1.5 and 8 MHz.

16. The device as set forth in claim 1, wherein the vascular probe is adapted to face the neck artery selected from the group consisting of a carotid artery and a vertebral artery, wherein a position and functional parameters of the vascular probe are amenable to detection and quantitative assessment of emboli passing through the neck artery before the emboli reaches a brain of the patient.

17. The device as set forth in claim 1, wherein the sensed closed parameter is communicated to the processor from the vascular probe by wireless communication between the vascular probe and the processor, wherein the wireless communication has an intermediate microprocessor located at a location comprising an area of compression of the compression member, a neck strap, or a surface of a neck compression collar.

18. A device for the prevention of stroke, comprising:
a processor;
a compression system;
a first compression member that is inflatable wherein a wall of the first compression member defines a void of the first compression member;
a first vascular probe that is carried by the first compression member and is imbedded into material of the first compression member that makes up the wall such that air or gas that goes into the void and inflates the first compression member comes into contact with the first vascular probe, and wherein the first vascular probe extends completely through the wall such that a portion of the first vascular probe is uncovered by the first compression member, wherein the first vascular probe is adapted to sense a parameter of a circulation system of a patient, wherein the parameter that is sensed is emboli present in a closed left carotid artery that is not being externally accessed when the parameter is sensed such that the parameter is a closed parameter, and wherein the sensed emboli closed parameter from the first vascular probe is communicated to the processor, wherein the processor processes the sensed emboli closed parameter from the first vascular probe and based upon this processing communicates with the compression system to instruct the compression system to actuate the first compression member;
a second compression member; and
a second vascular probe that is carried by the second compression member, wherein the second vascular probe is adapted to sense a parameter of the circulation system of the patient, wherein the parameter that is sensed is emboli present in a closed right carotid artery that is not being externally accessed when the parameter is sensed such that the parameter is a closed parameter, and wherein the sensed emboli closed parameter from the second vascular probe is communicated to the processor, wherein the processor processes the closed parameter from the second vascular probe and based upon this processing communicates with the compression system to instruct the compression system to actuate the second compression member;
wherein the first compression member and the second compression member are separated a distance from a center of the first compression member to a center of the second compression member that is the same distance as -a distance from the right carotid artery to the left carotid artery, when in use, along an anterior neck curvature of the patient;
wherein the first compression member, the first vascular probe, the second compression member, and the second vascular probe are adapted to be external to the interior of the patient when the first vascular probe senses the emboli present in the closed left carotid artery, and when the second vascular probe senses the emboli present in the closed right carotid artery;
wherein the first vascular probe is adapted to change position closer and farther relative to the closed left carotid artery and is adapted to change an orientation angle relative to the closed left carotid artery upon an increase in expansion of the first compression member upon actuation such that the sensed emboli closed parameter of the circulation system that is adapted to be sensed is sensed both before and after the change in position and the change in orientation angle;
wherein after the actuation of the first compression member the first vascular probe is configured to sense the disappearance of emboli in the left carotid artery and communicate the disappearance of emboli to the processor, wherein the processor processes the disappearance of emboli after the actuation of the first compression member and based upon this processing communicates with the compression system to instruct the compression system to remove actuation of the first compression member to remove the compression onto the left carotid artery;
wherein after the actuation of the second compression member the second vascular probe is configured to sense the disappearance of emboli in the right carotid artery and communicate the disappearance of emboli to the processor, wherein the processor processes the disappearance of emboli after the actuation of the second compression member and based upon this processing communicates with the compression system to instruct the compression system to remove actuation of the second compression member to remove the compression onto the right carotid artery.

19. The device as set forth in claim 18, further comprising a body and a strap that extends from the body and is adapted to wrap around a neck of the patient, wherein the body carries the first compression member within a first pocket of the body, wherein the compression system applies pressure to the first compression member when the compression system actuates the first compression member through inflation of the first compression member to force the first compression member towards the left carotid artery of the patient to compress the left carotid artery;
wherein the body carries the second compression member within a second pocket of the body, wherein the compression system applies pressure to the second compression member when the compression system actuates the second compression member through inflation of the second compression member to force the second compression member towards the right carotid artery of the patient to compress the right carotid artery.

20. The device as set forth in claim 18, wherein the first compression member when actuated creates a force that is adapted to extend in a direction of force to the closed left carotid artery, wherein the first vascular probe is adapted to emit a signal into the closed left carotid artery, wherein the first vascular probe is located on the first compression member such that the direction of the signal is not parallel to the direction of force and is oriented at an angle that is from 15 degrees-60 degrees to the direction of force.

21. The device as set forth in claim 18, further comprising:
a downstream vascular probe that is carried by the first compression member, wherein the downstream vascular probe is adapted to sense a parameter of the circulation system of the patient, wherein the parameter that is sensed by the downstream vascular probe is from the closed left carotid artery that is not being externally accessed when the parameter is sensed such that the parameter sensed by the downstream vascular probe is a closed parameter, and wherein the sensed closed parameter from the downstream vascular probe is communicated to the processor; and a middle vascular probe that is carried by the first compression member, wherein the middle vascular probe is adapted to sense a parameter of the circulation system of the patient, wherein the parameter that is sensed by the middle vascular probe is from the closed left carotid artery that is not being externally accessed when the parameter is sensed such that the parameter sensed by the middle vascular probe is a closed parameter, and wherein the sensed closed parameter from the middle vascular probe is communicated to the processor;

wherein actuation of the first compression member causes an area of compression to be imparted onto the closed left carotid artery, wherein the first vascular probe is adapted to be located upstream from the area of compression in the flow direction of the closed left carotid artery, wherein the downstream vascular probe is adapted to be located downstream from the area of compression in the flow direction of the closed left carotid artery, and wherein the middle vascular probe is adapted to be located at the area of compression of the closed left carotid artery.

22. The device as set forth in claim 18, wherein the parameter that is sensed by the first vascular probe is emboli present in the closed left carotid artery that is an intensity of a first embolic load that is represented by a number of embolic signals per second, and wherein the parameter that is sensed by the second vascular probe is emboli present in the closed right carotid artery that is an intensity of a second embolic load that is represented by a number of embolic signals per second, and wherein a degree of automated carotid compression in response to detected emboli is proportional to a degree of a calculated first embolic load and to a degree of a calculated second embolic load.

23. The device as set forth in claim 18, wherein the first vascular probe is located on a mobile portion of the first compression member that is adapted to change the orientation angle of the first vascular probe in relation to the left carotid artery from 0 to 90% depending on a degree of actuation of the first compression member.

24. A device for the prevention of stroke, comprising:
a processor;
a compression system;
a first compression member that is inflatable such that a first interior wall defines a first void of the first compression member;
a first vascular probe that is carried by the first compression member and is located inside of the first compression member and is imbedded into material of the first compression member that makes up the first interior wall such that air or gas that goes into the first void and inflates the first compression member comes into contact with the first vascular probe and wherein the first vascular probe extends completely through the first interior wall such that a portion of the first vascular probe is uncovered by the first interior wall, wherein the first vascular probe is adapted to sense a parameter of a circulation system of a patient from a closed left carotid artery that is not being externally accessed when the parameter is sensed such that the parameter is a closed parameter, and wherein the sensed closed parameter from the left carotid artery is communicated to the processor, wherein the processor processes the sensed closed parameter from the left carotid artery and based upon this processing communicates with the compression system to instruct the compression system to actuate the first compression member;
a second compression member that is inflatable such that a second interior wall defines a second void of the second compression member; and
a second vascular probe that is carried by the second compression member and is located inside of the second compression member so as to be located on the second interior wall, wherein the second vascular probe is adapted to sense a parameter of the circulation system of the patient from a closed right carotid artery that is not being externally accessed when the parameter is sensed such that the parameter is a closed parameter, and wherein the sensed closed parameter from the right carotid artery is communicated to the processor, wherein the processor processes the sensed closed parameter from the right carotid artery and based upon this processing communicates with the compression system to instruct the compression system to actuate the second compression member;
wherein the first compression member, the first vascular probe, the second compression member, and the second vascular probe are adapted to be external to the interior of the patient;
wherein the first compression member when actuated creates a force that is adapted to extend in a direction of force to the closed left carotid artery, wherein the first vascular probe is adapted to emit a signal into the closed left carotid artery, wherein the first vascular probe is located on the first compression member such that the direction of the signal is not parallel to the direction of force and is oriented at an angle that is from 15 degrees-60 degrees to the direction of force;
wherein the first vascular probe is adapted to change position closer and farther relative to the closed left carotid artery and is adapted to change an orientation angle relative to the closed left carotid artery upon an increase in expansion of the first compression member such that the parameter of the circulation system that is adapted to be sensed is sensed both before and after the change in position and the change in orientation angle.

* * * * *